US009028863B2

(12) United States Patent
Kester et al.

(10) Patent No.: US 9,028,863 B2
(45) Date of Patent: May 12, 2015

(54) METHOD AND SYSTEM FOR SYSTEMIC DELIVERY OF GROWTH ARRESTING, LIPID-DERIVED BIOACTIVE COMPOUNDS

(75) Inventors: Mark Kester, Harrisburg, PA (US); Thomas Stover, Hershey, PA (US); Tao Lowe, Hershey, PA (US); James H. Adair, State College, PA (US); Young Shin Kim, Hershey, PA (US)

(73) Assignee: The Penn State Research Foundation, University Park, PA (US)

( * ) Notice: Subject to any disclaimer, the term of this patent is extended or adjusted under 35 U.S.C. 154(b) by 2672 days.

(21) Appl. No.: 10/835,520

(22) Filed: Apr. 26, 2004

(65) Prior Publication Data

US 2005/0025820 A1 Feb. 3, 2005

Related U.S. Application Data

(60) Provisional application No. 60/465,938, filed on Apr. 25, 2003, provisional application No. 60/465,937, filed on Apr. 28, 2003.

(51) Int. Cl.
| | | |
|---|---|---|
| *A61K 31/164* | (2006.01) | |
| *A61K 47/48* | (2006.01) | |
| *A61K 9/51* | (2006.01) | |
| *B82Y 5/00* | (2011.01) | |
| *A61K 48/00* | (2006.01) | |
| *A61K 9/50* | (2006.01) | |
| *A61K 47/02* | (2006.01) | |
| *A61K 9/127* | (2006.01) | |

(52) U.S. Cl.
CPC ............ *A61K 31/164* (2013.01); *A61K 9/5115* (2013.01); *A61K 9/501* (2013.01); *A61K 47/02* (2013.01); *A61K 9/1271* (2013.01); *A61K 9/1272* (2013.01); *A61K 9/51* (2013.01); *A61K 47/482* (2013.01); *A61K 47/48215* (2013.01); *A61K 47/48315* (2013.01); *A61K 48/00* (2013.01); *B82Y 5/00* (2013.01); *Y10S 977/783* (2013.01); *Y10S 977/907* (2013.01)

(58) Field of Classification Search
None
See application file for complete search history.

(56) References Cited

U.S. PATENT DOCUMENTS

| | | | | |
|---|---|---|---|---|
| 5,223,263 | A | | 6/1993 | Hostetler |
| 5,591,453 | A | * | 1/1997 | Ducheyne et al. ............ 424/484 |
| 5,681,589 | A | * | 10/1997 | Wei et al. ..................... 424/450 |
| 6,395,713 | B1 | | 5/2002 | Beigelman |
| 6,426,067 | B1 | | 7/2002 | Matthews |
| 6,491,903 | B1 | | 12/2002 | Forster |
| 6,832,735 | B2 | * | 12/2004 | Yadav et al. ..................... 241/16 |
| 2004/0101822 | A1 | * | 5/2004 | Wiesner et al. .................... 435/5 |
| 2005/0169882 | A1 | | 8/2005 | Lowe et al. |

FOREIGN PATENT DOCUMENTS

| | | | |
|---|---|---|---|
| JP | 10-506395 | A | 6/1998 |
| JP | 10-510805 | A | 10/1998 |
| JP | 2002-533394 | A | 10/2002 |
| WO | 9521175 | A1 | 8/1995 |
| WO | 9532002 | A1 | 11/1995 |
| WO | 9603117 | A1 | 2/1996 |
| WO | 9610391 | A1 | 4/1996 |
| WO | WO 96/10392 | A1 | 4/1996 |
| WO | WO 96/18404 | A1 | 6/1996 |
| WO | 9904819 | A1 | 2/1999 |
| WO | 9938542 | A1 | 8/1999 |
| WO | WO 00/38681 | A1 | 7/2000 |
| WO | 0045791 | A2 | 8/2000 |
| WO | WO 01/88540 | * | 11/2001 |
| WO | WO 03020320 | A2 * | 3/2003 |

OTHER PUBLICATIONS

Jain et al. Journal of the American Chemical Society 1998 120:11092-11095.*
Falaize et al. Journal of the American Ceramic Society 1999 82:969-97.*
Labhasetwar et al. Advanced Drug Delivery Reviews 1997 24:63-85.*
Charles et al. Circulation Research 2000 87:282-288.*
Weimer et al. Journal of Biochemical and Biophysical Methods 2000 45:211-219.*
Soltys et al. Biomaterials 2000 21:37-48.*
Schmidt et al. Advanced Materials 2004 14:532-535.*
Anee et al. Materials Chemistry and Physics 2003 80:725-730 availabe online Mar. 12, 2003.*
Supplementary European Search Report, Application No. EP 04 76 0381, dated Sep. 21, 2011.
English Abstract of JP 09-110722, published Apr. 28, 1997.
The Penn State Research Foundation, JP 2010-262287, Hiraki & Associates, Foreign Associate Search Results letter dated Jan. 9, 2013.

* cited by examiner

*Primary Examiner* — Juliet Switzer
*Assistant Examiner* — Caralynne Helm
(74) *Attorney, Agent, or Firm* — McKee, Voorhees & Sease, P.L.C.

(57) ABSTRACT

A system and method for optimizing the systemic delivery of growth-arresting lipid-derived bioactive drugs or gene therapy agents to an animal or human in need of such agents utilizing nanoscale assembly systems, such as liposomes, resorbable and non-aggregating nanoparticle dispersions, metal or semiconductor nanoparticles, or polymeric materials such as dendrimers or hydrogels, each of which exhibit improved lipid solubility, cell permeability, an increased circulation half life and pharmacokinetic profile with improved tumor or vascular targeting.

14 Claims, 20 Drawing Sheets

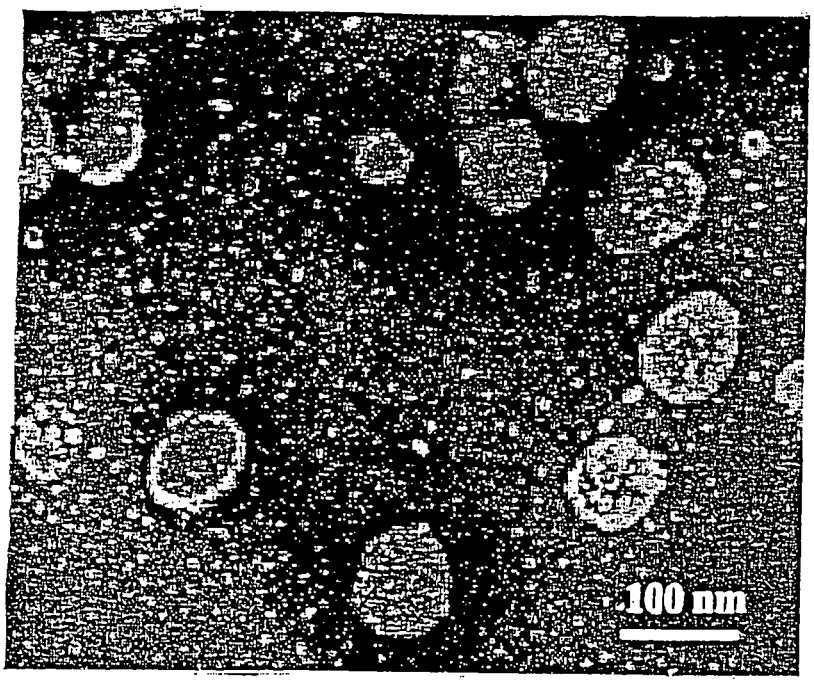
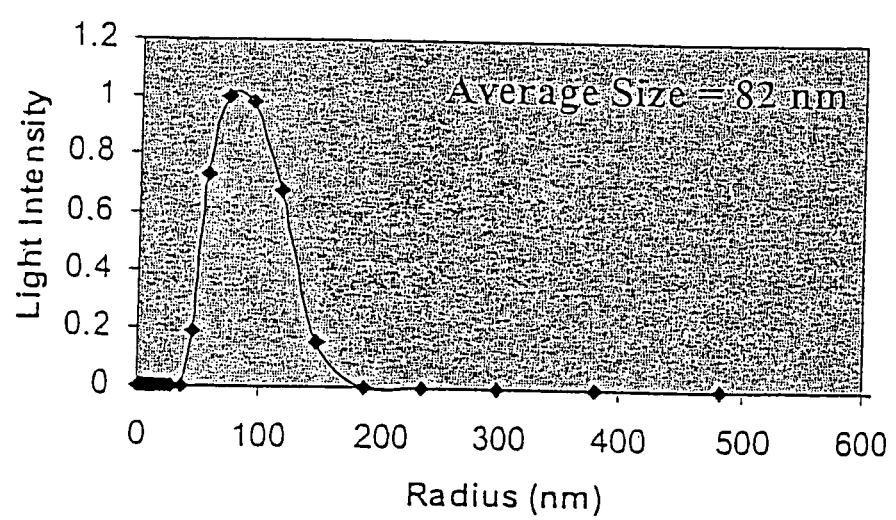
Fig. 2A-B

C 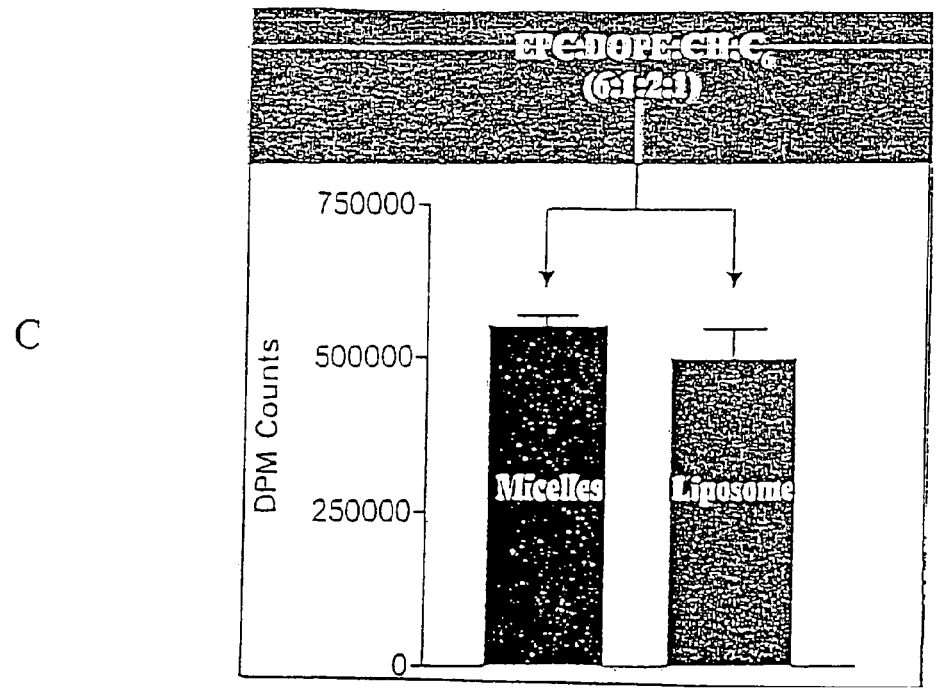
D 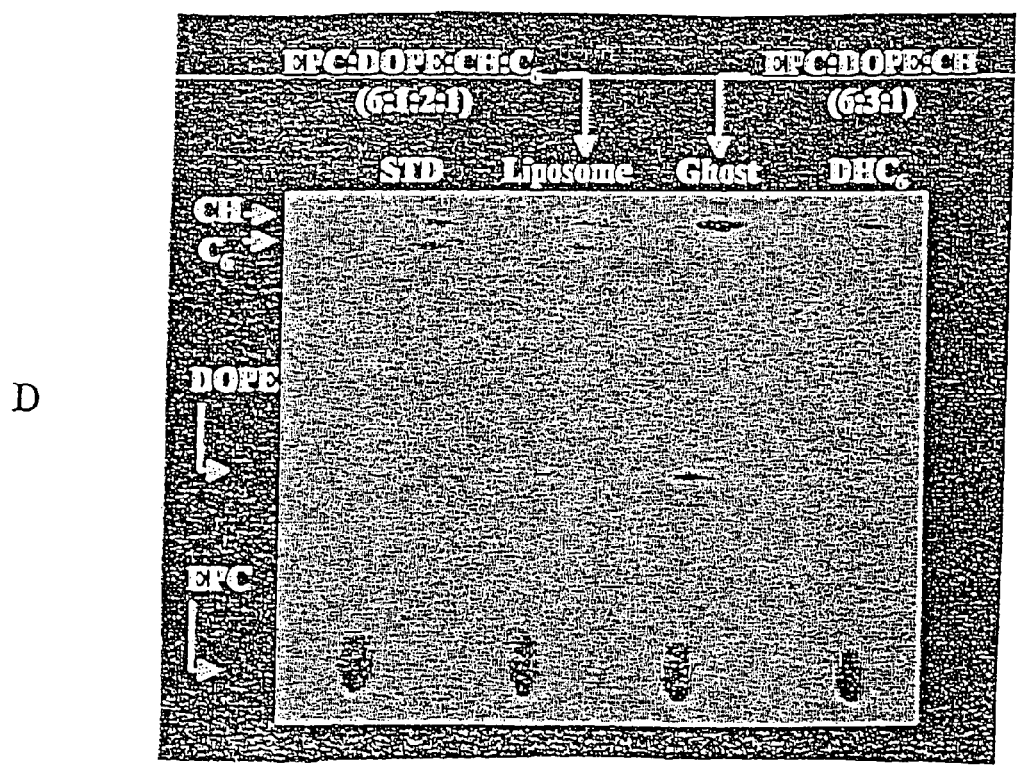
Fig. 2C-D

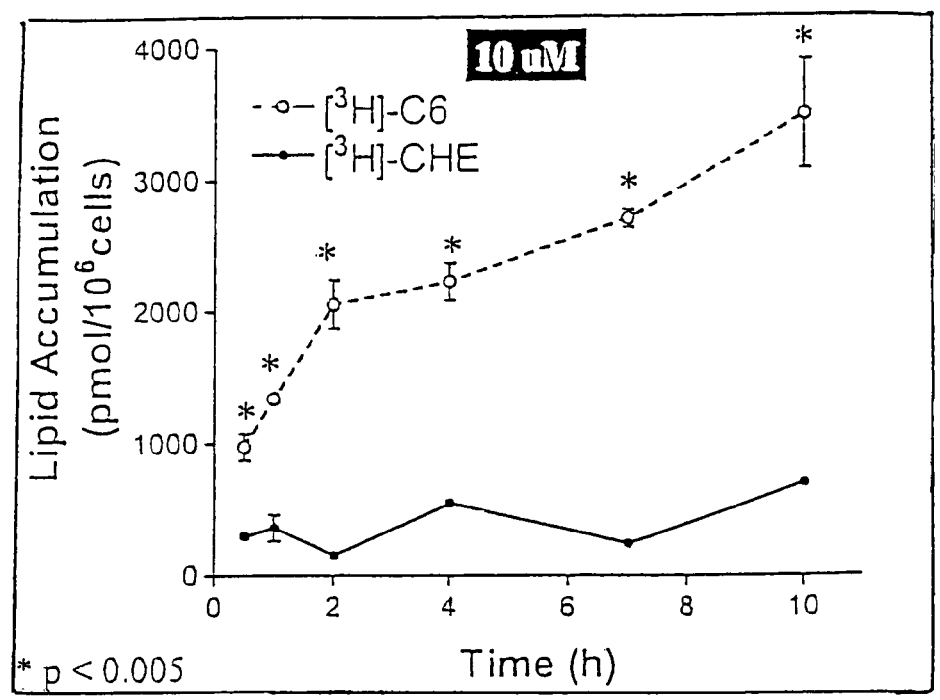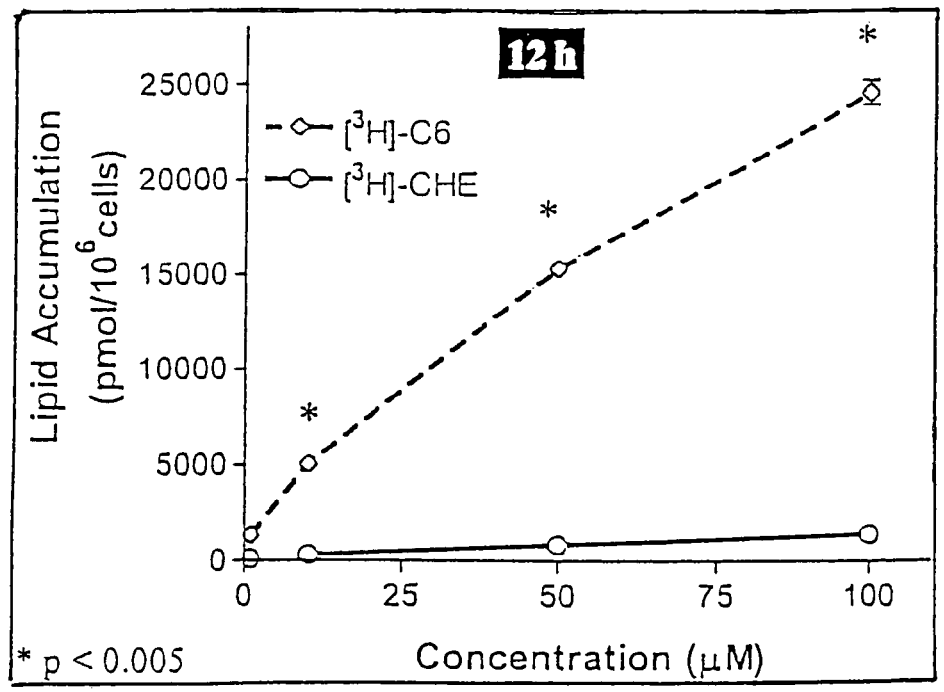
Fig. 3B-C

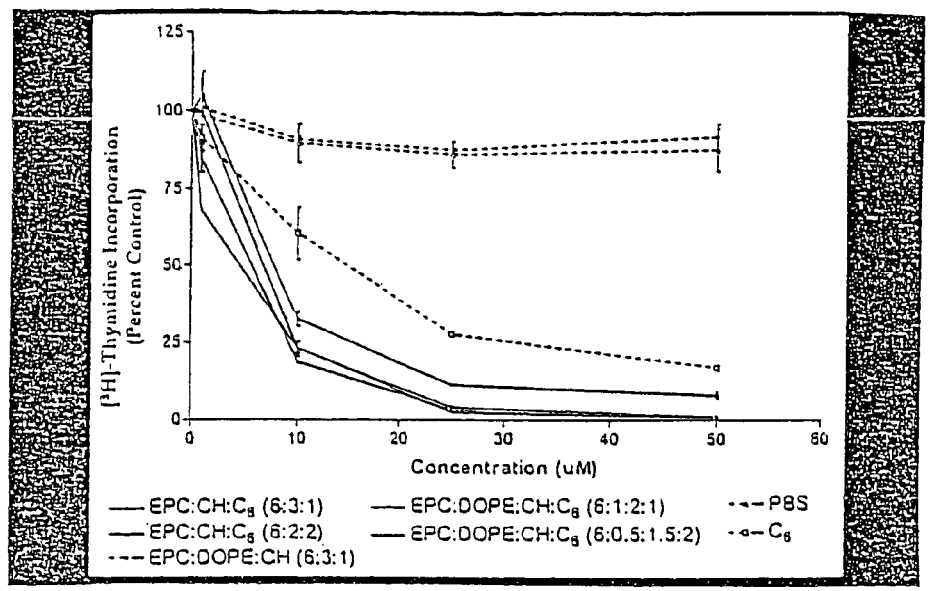
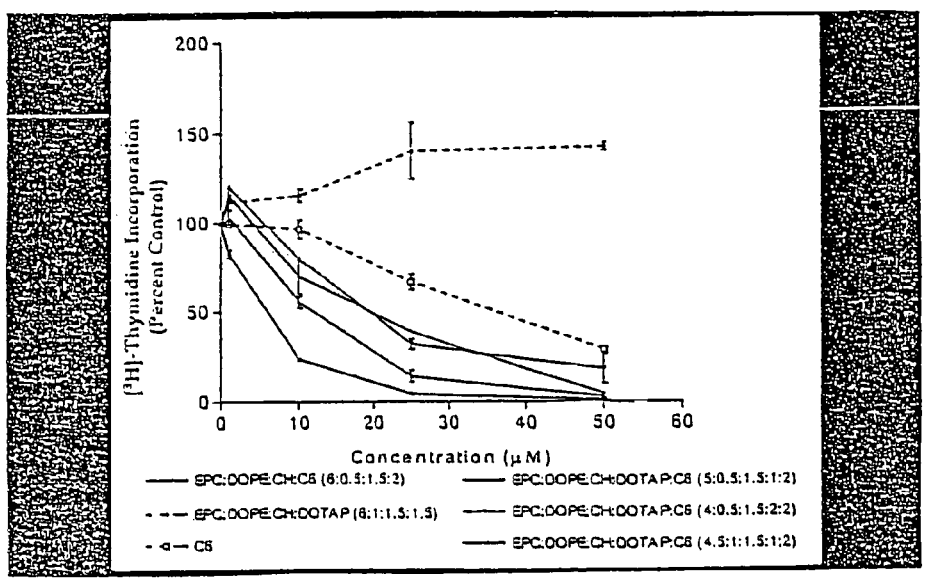
Fig. 4A-B

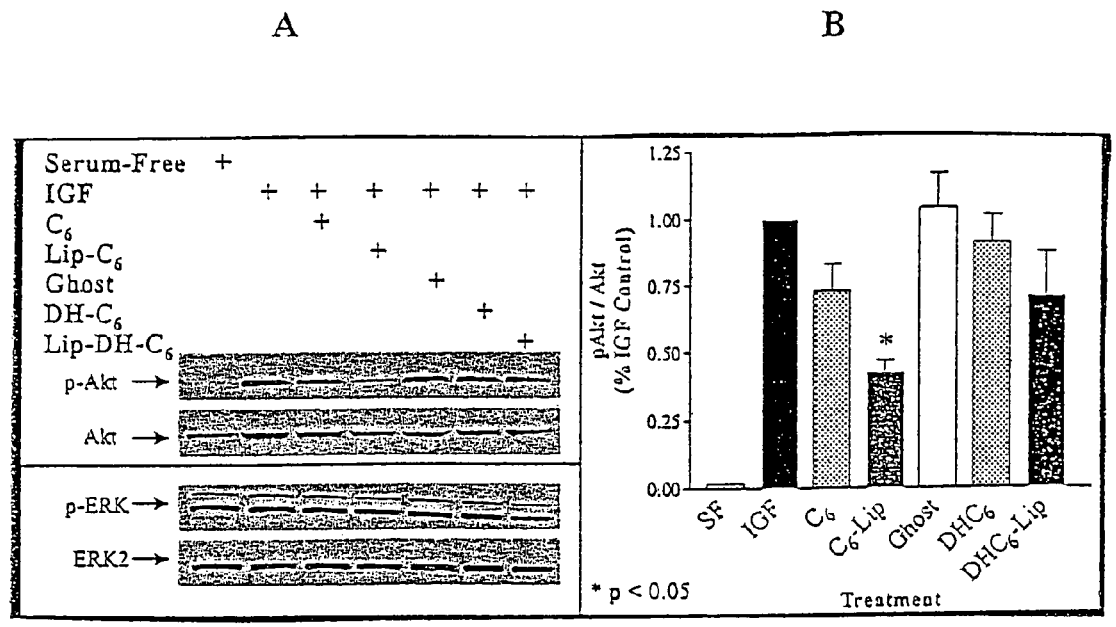
Fig. 8A-B

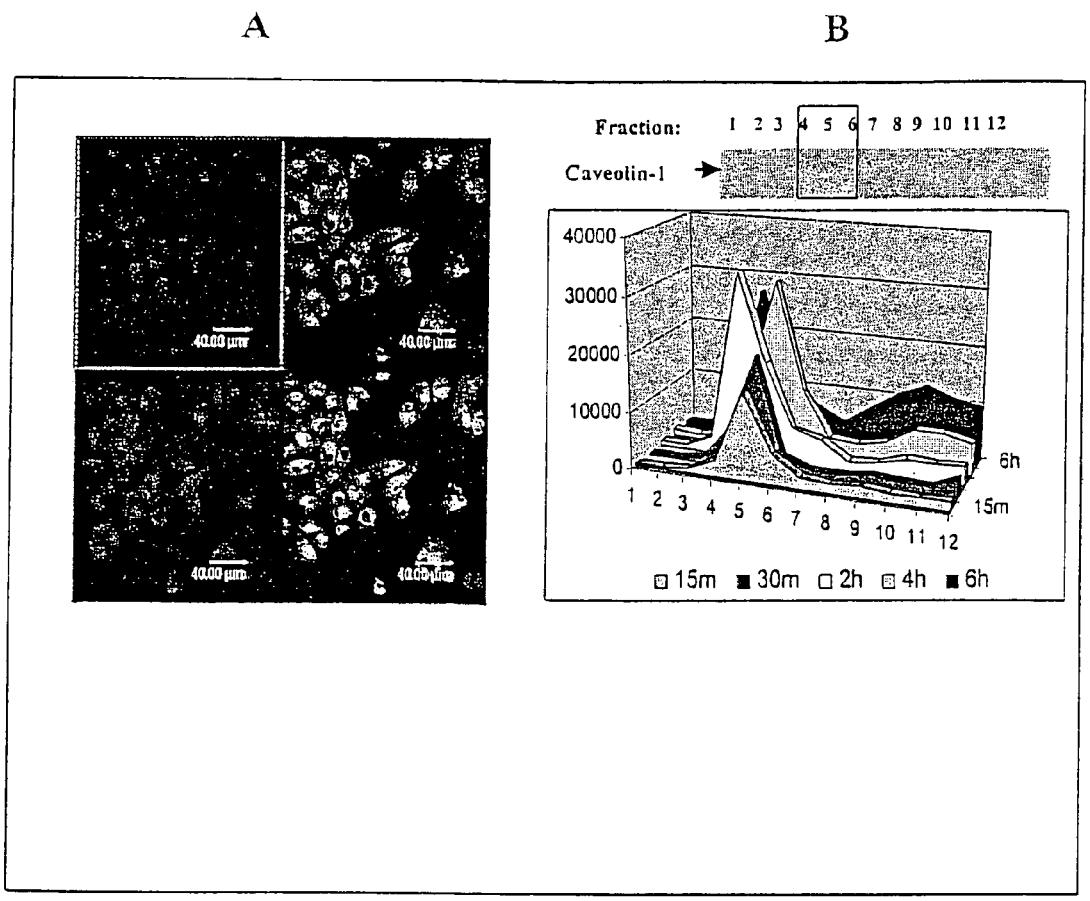
Fig. 9A-B

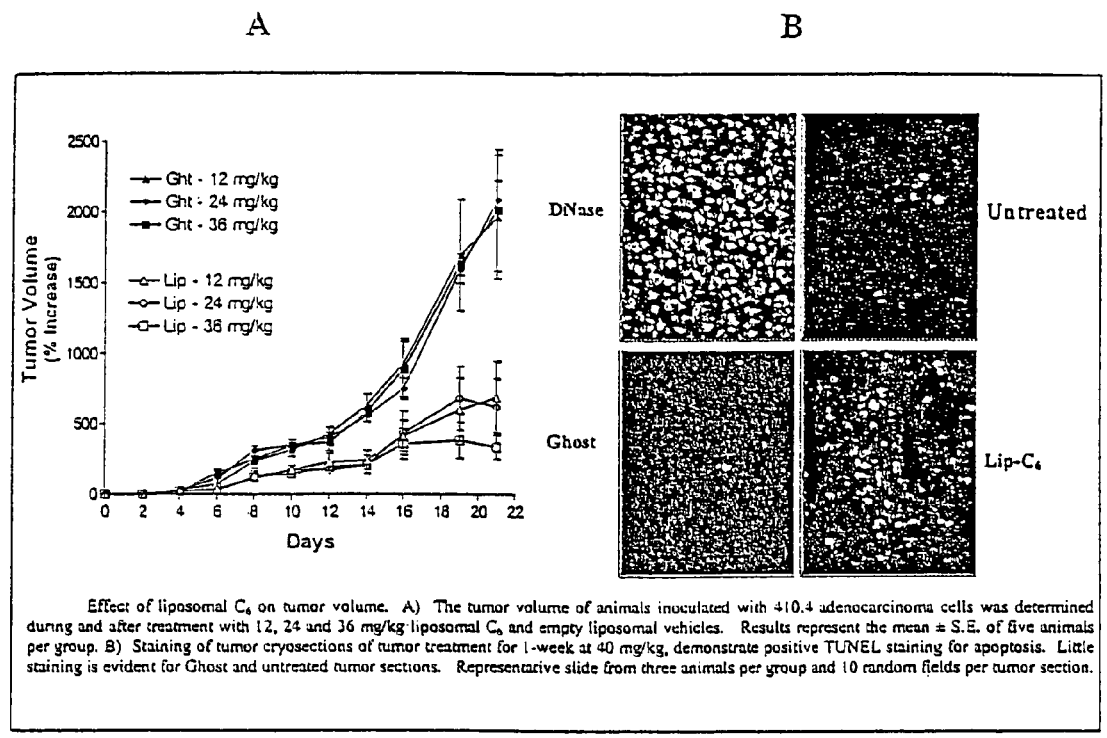
Fig. 10A-B

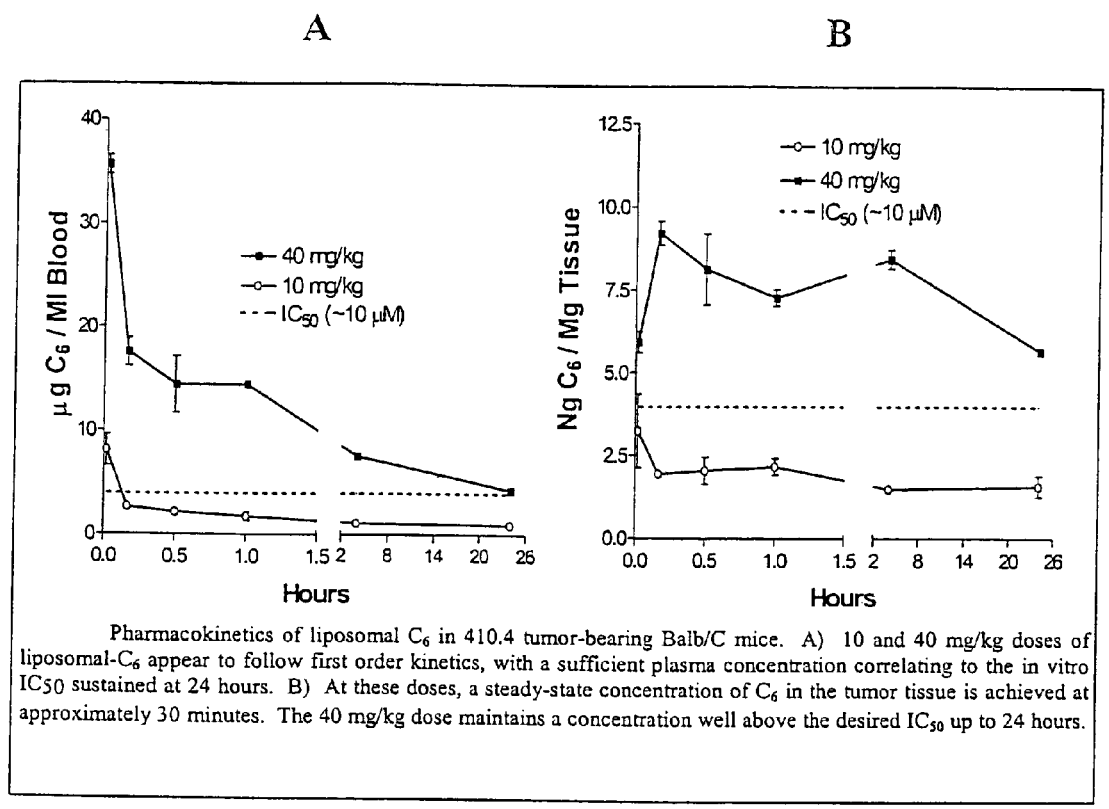
Fig. 11A-B

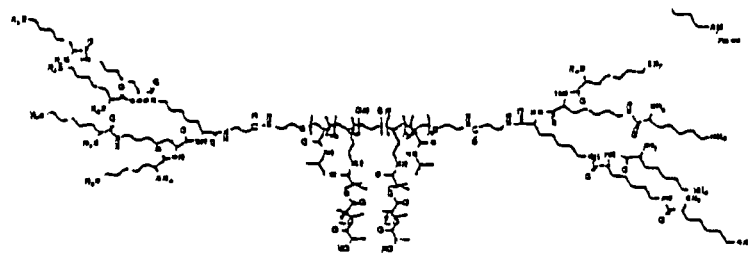
Fig. 12. Proprietary dendritic structure composed of PLL, PLLA, and NIPAAM polymers that have thermo-responsive and biodegradable properties.

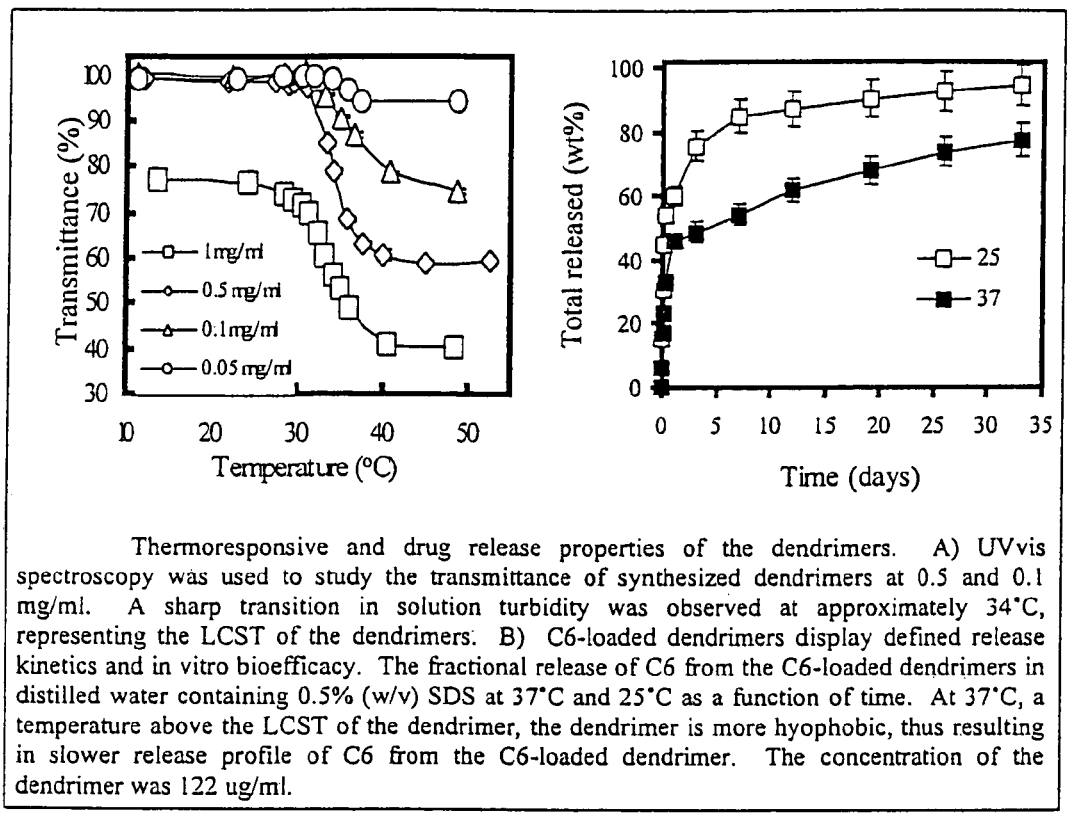

Thermoresponsive and drug release properties of the dendrimers. A) UVvis spectroscopy was used to study the transmittance of synthesized dendrimers at 0.5 and 0.1 mg/ml. A sharp transition in solution turbidity was observed at approximately 34°C, representing the LCST of the dendrimers. B) C6-loaded dendrimers display defined release kinetics and in vitro bioefficacy. The fractional release of C6 from the C6-loaded dendrimers in distilled water containing 0.5% (w/v) SDS at 37°C and 25°C as a function of time. At 37°C, a temperature above the LCST of the dendrimer, the dendrimer is more hyophobic, thus resulting in slower release profile of C6 from the C6-loaded dendrimer. The concentration of the dendrimer was 122 ug/ml.

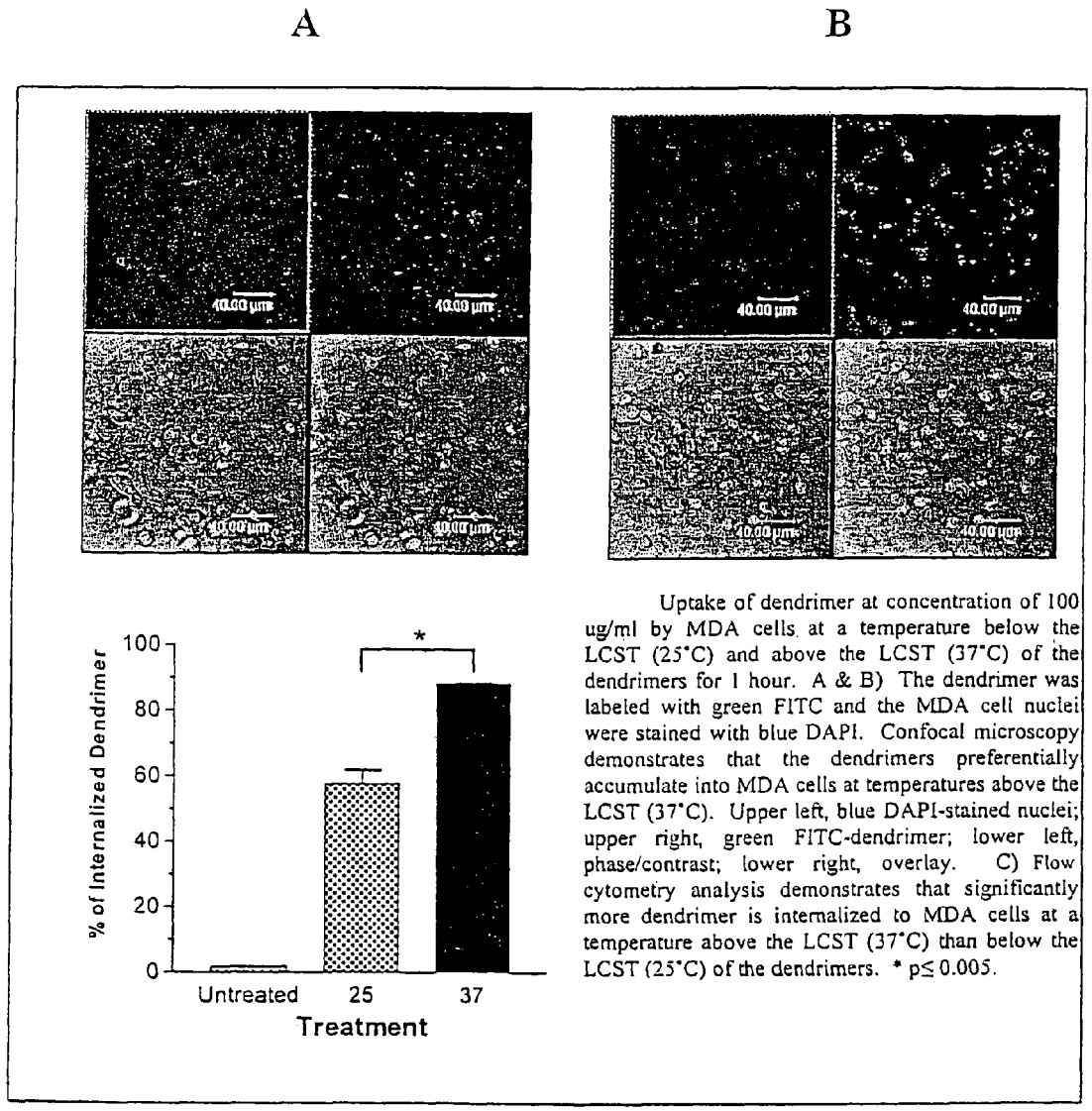
Fig. 14A-C

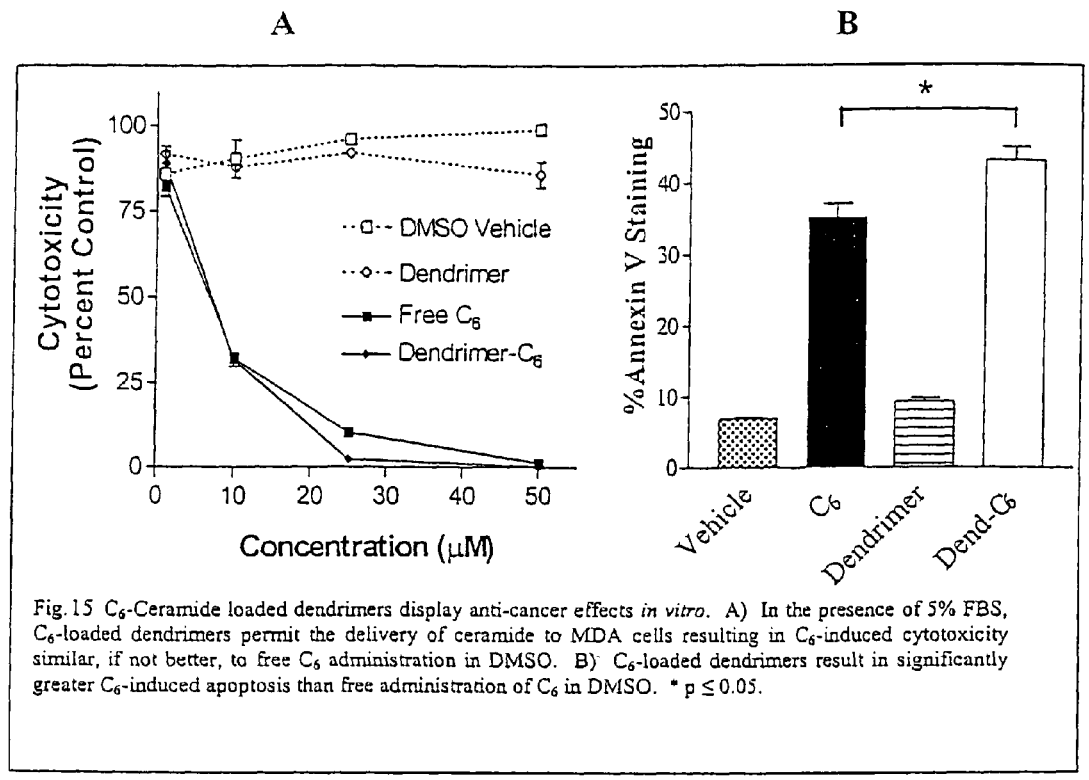

Fig. 15 $C_6$-Ceramide loaded dendrimers display anti-cancer effects *in vitro*. A) In the presence of 5% FBS, $C_6$-loaded dendrimers permit the delivery of ceramide to MDA cells resulting in $C_6$-induced cytotoxicity similar, if not better, to free $C_6$ administration in DMSO. B) $C_6$-loaded dendrimers result in significantly greater $C_6$-induced apoptosis than free administration of $C_6$ in DMSO. * $p \leq 0.05$.

Fig. 15A-B

METHOD AND SYSTEM FOR SYSTEMIC DELIVERY OF GROWTH ARRESTING, LIPID-DERIVED BIOACTIVE COMPOUNDS

The present application claims priority to U.S. Provisional Application No. 60/465,938, filed Apr. 25, 2003, which is incorporated herein by reference.

BACKGROUND OF THE INVENTION

1. Field of the Invention

The present invention relates to the field of nanotechnology. More particularly, the present invention provides nanoscale assembly systems for systemic delivery of therapeutic bioactive lipid compounds and/or hydrophobic chemotherapeutic agents and/or nucleotide/gene agents to individuals in need of such therapy.

2. Description of Related Art

Nanotechnology has been intricately linked with the life sciences (generally referred to as nanobiotechnology) since its inception by Richard Keynman in his 1959 speech, "There's Plenty of Room at the Bottom," in which he made reference to the complexity and smallness of the living cell and challenged the scientific community to "make a thing very small which does what we want" (Feynman, R. P., 1959, available: www.zyvex.com/nanotech/feynman.html). Although commercial nanobiotechnology is still in its infancy, the rate of nanoscale assembly system development has been increasing exponentially in the last ten years, due to the unique advantages that these systems offer for drug delivery and therapeutics. Examples of some nanoscale assembly systems include liposomes, polymeric structures such as dendrimers and hydrogels, and metal or semiconductor nanoparticles referred to as quantum dots.

Many effective reagents are available for introducing transcriptionally active DNA, and even functional peptides and proteins into viable cells. However, approaches to deliver bioactive lipids into living cells are not generally available. The delivery of bioactive sphingolipids and phospholipid metabolites, analogues, mimetics or derivatives and their intercalation into cells is impeded by their physical-chemical properties that render these lipids hydrophobic and cell impermeable.

Ceramide, a sphingolipid that acts as a lipid-derived second messenger that modulates the induction of cell differentiation, cell cycle arrest and/or apoptosis, is an example of a bioactive lipid whose exogenous administration has been problematic. Intracellular ceramide accumulation results from multiple stimuli, such as growth factor deprivation, cytokines, chemotherapy and other cytotoxic agents, ionizing radiation, heat shock, and various environmental factors. These stimuli have been observed to initiate ceramide-mediated signaling cascades, including the inhibition of Akt pro-survival pathways and the stimulation of caspase activity, which ultimately leads to DNA fragmentation and cell death. Thus, based on ceramide's potent regulation of cell growth, differentiation, and death, and the fact that it is a natural molecule that targets discrete kinases and signaling pathways linked to proliferation and/or survival, ceramide has been identified as a therapeutic agent in cancer and cardiovascular disease.

The clinical utility of local delivery of a cell-permeable ceramide analogue, $C_6$, from drug-eluting platforms previously has been demonstrated by Charles et al. (Circ. Res. 2000 Aug. 18:87(4):282-8). Specifically, ceramide-coated balloon catheters were shown to induce cell cycle arrest in stretch-injured vascular smooth muscle cells. Although the delivery of $C_6$-ceramide from coated and distended balloons allow for direct delivery to the vasculature, there are several obstacles to the delivery of ceramide for systemic applications, such as cancer chemotherapy or targeting diffuse atherosclerotic lesions and vulnerable plaque. In particular, three significant barriers to systemic ceramide delivery exist, despite the use of short chain, more cell permeable derivatives.

First, short-chain, cell-permeable ceramide analogues such as $C_2$, $C_6$, and $C_8$-ceramide are still lipids, and thus extremely hydrophobic by nature, precipitating as fine lipid micelle suspensions when added, in DMSO or ethanol vehicle, to cell media. Second, although short-chain ceramide analogues are more cell-permeable than long-chain physiological ceramide ($C_{18}$-$C_{24}$-ceramide), their sphingoid backbone limits their intercalation into plasma membranes. Finally, the existence of circulating and intracellular ceramidases promote the conversion of bioactive ceramides into less pro-apoptotic metabolites.

Organic solvent systems have been investigated in order to augment the delivery of ceramide to cells. It has been proposed that a dodecane/ethanol solvent system, which is insoluble in culture media, precipitates out with the ceramide and forms very small droplets, or micelles, that fuse with the plasma membrane. The use of such precipitating solvents may be limited by the variability in particle size and access to cellular membranes. Protein adjuvants, such as bovine serum albumin, may also assist in vitro ceramide delivery via non-specific lipid/protein interactions, but would not permit the efficient delivery of sufficient quantities of $C_6$-ceramide to systemic targets.

Thus, in order to realize the therapeutic benefits of bioactive lipids or gene therapy agents, there exists a need for improved systemic delivery systems of such hydrophobic or charged chemotherapeutic compounds into living cells of animals or humans in need of such therapy.

SUMMARY OF THE INVENTION

The present invention addresses this critical need by providing a system and method for optimizing the systemic delivery of growth-arresting, pro-apoptotic, lipid-derived bioactive drugs and/or chemotherapeutic hydrophobic agents and/or gene therapy agents to an animal or human in need of such agents utilizing nanoscale assembly systems.

The present invention provides a method and system for maximizing the systemic delivery of growth-arresting, pro-apoptotic, lipid-derived bioactive therapeutic compounds and/or gene therapy agents to living cells of an animal or human in need of such therapy, utilizing nanoscale assembly systems, such as liposomes, resorbable and non-aggregating dispersed nanoparticles, metal or semiconductor nanoparticles or polymeric materials such as dendrimers or hydrogels, each of which exhibit improved lipid solubility, cell permeability, an increased circulation half life and pharmacokinetic profile with improved tumor or vascular targeting.

In one embodiment of the present invention, polyethyleneglycol 450 liposomes suitable for delivery of bioactive lipids, proteins and therapeutic agents, referred to herein as "pegylated" liposomes are formulated that have one or more membranes comprised of a growth-arresting lipid-derived bioactive compound and/or a gene therapy agent and/or cholesterol. These pegylated liposomes have been formulated to contain PEG C8 (pegylated cell-permeable ceramide), ranging in size between 750-5000 MW and/or PEG DSPE (disteroylphosphatidylethanolamine) ranging in size between 2000-5000 MW. The present embodiment uses PEG C8 to stabilize the lipid bilayer, allowing the liposome to contain high molar ration (i.e., 30%) of free bioactive C6 ceramide. In addition, the embodiment utilizes the PEG C8 as an integral component of the liposome that contains the bioactive ceramide and/or a hydrophobic chemotherapeutic agent and/or a gene therapy agent. Moreover, PEG-C8 formulated liposomes ensures optimal intercalation and localization of the free ceramide into caveolin-rich lipid rafts, a prerequisite for membrane internalization and transfer to subcellular organelles including the mitochondria for subsequent induction of apoptosis or programmed cell death of the targeted tissue or tumor. The pegylated liposomes, also known as "stealth" liposomes, are capable of evading clearance from the circulation by the reticuloendothelial system (RES), leading to improved circulation half life and tissue targeting. Targeting can be further achieved via the conjugation of particular targeting moieties, such as antibodies and/or receptor ligands, which will promote the targeted accumulation into specific cells or tissues of the body. Additional embodiments assert that lipid therapeutics can also be formulated into "cationic" liposomes comprised of cationic lipids, in the presence or absence of PEG-$C_8$, for effectively delivering negatively charged oligonucleotides; or as "fusogenic" liposomes, in the presence or absence of PEG-$C_8$, where the entire membrane of the liposome fuses with the cell membrane of the target site to deliver the constituents and contents of the liposome therein.

In another embodiment of the present invention, resorbable nanoparticles having a calcium phospho-silicate (CPS) shell are provided, in which growth arresting, proapoptotic, lipid-derived bioactive compounds, and/or chemotherapeutic hydrophobic agents, and/or gene therapy agents are loaded into the resorbable nanoparticles. The resorbable nanoparticles of the present invention can deliver chemotherapeutic hydrophobic lipids or drugs or gene therapeutic agents systemically to living cells, which normally are not transportable through the circulation. A key feature of the synthesis of the resorbable nanoparticles is the proper dispersion (non-aggregation) of the nanoparticles in an aqueous liquid medium. One way to achieve dispersion is the use of size exclusion high performance liquid chromatography (SEC) modified specifically for the silicate-containing shell nanoparticles. Another way to achieve dispersion of the nanoparticles is to attach organic, inorganic or metal-organic dispersants to the outer CPS shell. Additionally, a carbodiimide-mediated polyethylene glycol (PEG) coupling agent can be attached to the alkylamine silane or alkylcarboxylic acid coupling agent to further ensure the "dispersed" non-aggregating state of the nanoparticles in vivo and to provide an conjugation point for targeting moieties onto the PEG coupling agent, thus enabling the nanoparticles to target specific sites for intracellular drug delivery.

In a further embodiment of the present invention, individual polymers can be combined to form materials which are both "bio-smart", i.e. respond to physical or chemical stimuli, and biodegradable in vivo and which can be loaded with the growth-arresting, lipid-derived bioactive compounds and/or gene therapy agents.

BRIEF DESCRIPTION OF THE DRAWINGS

FIGS. 2A-B. Characterization of liposomal formulations. Liposomal formulations are produced with a spherical morphology and a homogeneous size distribution. (A) Representative TEM of pegylated liposomal vesicles [DOPC/DOPE/CH/PEG-$C_8$/C6 (4:3:1:1:1)]. Identical micrographs were observed with conventional liposomal formulations [EPC/DOPE/CH/$C_6$ (6:0.5:1.5:2)] (data not shown). Vesicular size was between 85 and 140 nm in diameter; bar represents 100 nm. Extrusion of lipid solutions does not significantly diminish $C_6$ incorporation into liposomal vesicles. (B) Illustration of the average size of the liposomal formulations.

FIGS. 2C-D. Characterization of liposomal formulations. (C) Micelle formulations in a final concentration of 10 mg/ml, composed of EPC/DOPE/CH/C6 (6:0.5:1.5:2) along with trace amounts of [$^3$H]$C_6$ that were subjected to extrusion to produce conventional liposomes as described. Mean±S.E., n=3 separate experiments. Lipid composition remains consistent following extrusion of lipid micelle solution to produce liposomal vesicles. (D) Representative TLC of conventional liposomal formulations [EPC/DOPE/CH/C6 (3.5:3:2:1.5) and EPC/DOPE/CH/DHC$_6$ (3.5:3:2:1.5)] separated using a CHCL$_3$/MeOH/ddH$_2$O (60:25:5) solvent system. As expected, $C_6$ but not DHC$_6$ was stained with iodine due to the lack of the $C_{4-5}$ double bond of DHC$_6$.

FIGS. 3B-C. In vitro pharmacokinetics of $C_6$ delivery. Illustration that liposomal $C_6$, but not Cholesteryl-1,2-$^3$H(N) hexadecyl ether (3H-CHE) partitions into MDA cell membranes as a function of time (B) and dose (C). Pegylated liposomes [DOPC/DOPE/CH/PEG-C8/$C_6$ (4:3:1:1:1)] were formulated with trace amounts of [$^3$H $C_6$] and [$^3$H CHE] to evaluate the mechanism of ceramide (10 μM) delivery to MDA cells at the indicated time periods. A dose-dependent mechanism of ceramide delivery was examined over a 10-h treatment period. The mass of lipid delivered to cells was calculated as pmol/$10^6$ cells. Mean±S.E., n=3 separate experiments. *, p<0.05 when comparing $C_6$ accumulation with CHE accumulation in respective formulations.

FIGS. 4A-B. Thymidine incorporation growth assays showing that liposomal $C_6$ delivery is more potent than non-liposomal $C_6$ in estrogen receptor-negative MDA breast cancer cells. (A) conventional liposomes; (B) cationic liposomes.

FIGS. 8A-B. Liposomal $C_6$ delivery modulates signaling cascades associated with growth inhibition and/or apoptosis. Liposomal $C_6$ delivery inhibits Akt phosphorylation in MDA cells. (A and B) Cells were pretreated with nonliposomal $C_6$ (50 μM), pegylated liposomal $C_6$ [DOPC/DOPE/CH/PEG-C8/$C_6$ (4:3:1:1:1)] (50 μM), or Ghost liposome for 8 h and then stimulated with 20 ng/ml IGF-1 for an additional 15 min. Protein lysates were probed for both native and active (phosphorylated) forms of Akt. (A) Representative blot of n=3 separate experiments. (B), mean±S.E., n=3 separate experiments. *, p<0.05 when compared with untreated IGF-stimulated control.

FIGS. 9A-B. Liposomal C6 delivery results in the accumulation of C6 into caveolae and mitochondrial structures. (A) Confocal microscopic images of NBD-C6 delivery to cells from liposomal vesicles demonstrates that C6 also accumulates into cellular mitochondria. NBD-C6 co-localized with mitochondria. (B) Using [$^3$H]-C6 as a marker for total C6, pegylated liposomal delivery results in a time-dependent accumulation of ceramide in caveolae lipid signaling rafts. Ceramide accumulated in fractions #4-5 of a sucrose gradient, which represent caveolin-1 enriched lipid rafts (caveolae).

FIGS. 10A-B. Effect of pegylated liposomal $C_6$ [DSPC/DOPE/DSPC-PEG(5000)/C8-PEG(750)/$C_6$-Cer (3.75:1.75:0.75:0.75:3.0)] on tumor volume. (A) The tumor volume of animals inoculated with 410.4 adenocarcinoma cells was determined during and after treatment with 12, 24 and 36 mg/kg liposomal $C_6$ and empty liposomal vehicles. Results represent the mean±S.E. of five animals per group. (B) Staining of tumor cryosections of tumor treatment for 1-week at 40 mg/kg, demonstrate positive TUNEL staining for apoptosis. Little staining is evident for Ghost and untreated tumor sections. Representative slide from three animals per group and 10 random fields per tumor section.

FIG. 11A-B. Pharmacokinetics of pegylated liposomal C6 in 410.4 tumor bearing Balb/C mice. (A) 10 and 40 mg/kg doses of liposomal-C6 appear to follow first order kinetics, with a sufficient plasma concentration correlating to the in vitro IC50 sustained at 24 hours. (B) At these doses, a steady-state concentration of C6 in the tumor tissue is achieved at approximately 30 min. The 40 mg/kg dose maintains a concentration well above the desired IC50 up to 24 hours.

FIG. 12. Proprietary dendritic structure composed of PLL, PLLA, and NIPAAM polymers that have thermo-responsive and biodegradable properties.

FIG. 13A-B. Thermoresponsive and drug release properties of the dendrimers. A) Uvvis spectroscopy was used to study the transmittance of synthesized dendrimers at 0.5 and 0.1 mg/ml. A sharp transition in solution turbidity was observed at approximately 34° C., representing LCST of the dendrimers. B) $C_6$-loaded dendrimers display defined release kinetics and in vitro bioefficacy. The fractional release of $C_6$ from the $C_6$-loaded dendrimers in distilled water containing 0.5% (w/v) SDS at 37° C. and 25° C. as a function of time. At 37° C., a temperature above the LCST of the dendrimer, the dendrimer is more hydrophobic, thus resulting in slower release profile of $C_6$ from the $C_6$-loaded dendrimer. The concentration of the dendrimer was 122 ug/ml.

FIGS. 14A-C. Uptake of dendrimer at concentration of 100 ug/ml by MDA cells at a temperature below the LCST (25° C.) and above the LCST (37° C.) of the dendrimers for 1 hour. A & B) The dendrimer was labeled with green FITC and the MDA cell nuclei were stained with blue DAPI. Confocal microscopy demonstrates that the dendrimers preferentially accumulate into MDA cells at temperatures above the LCST (37° C.). Upper left, blue DAPI-stained nuclei; upper right, green FITC-dendrimer; lower left, phase/contrast; lower right, overlay. C) Flow cytometry analysis demonstrates that significantly more dendrimer is internalized to MDA cells at a temperature above the LCST (37° C.) than below the LCST (25° C.) of the dendrimers. *p≤0.005.

FIG. 15A-B. $C_6$-Ceramide loaded dendrimers display anticancer effects in vitro. A) In the presence of 5% FBS, $C_6$-loaded dendrimers permit the delivery of ceramide to MDA cells resulting in $C_6$-induced cytotoxicity similar, if not better, to free $C_6$ administration in DMSO. B) $C_6$-loaded dendrimers result in significantly greater $C_6$-induced apoptosis than free administration of $C_6$ in DMSO. *p≤0.05.

DESCRIPTION OF THE PREFERRED EMBODIMENTS

Figure 1:
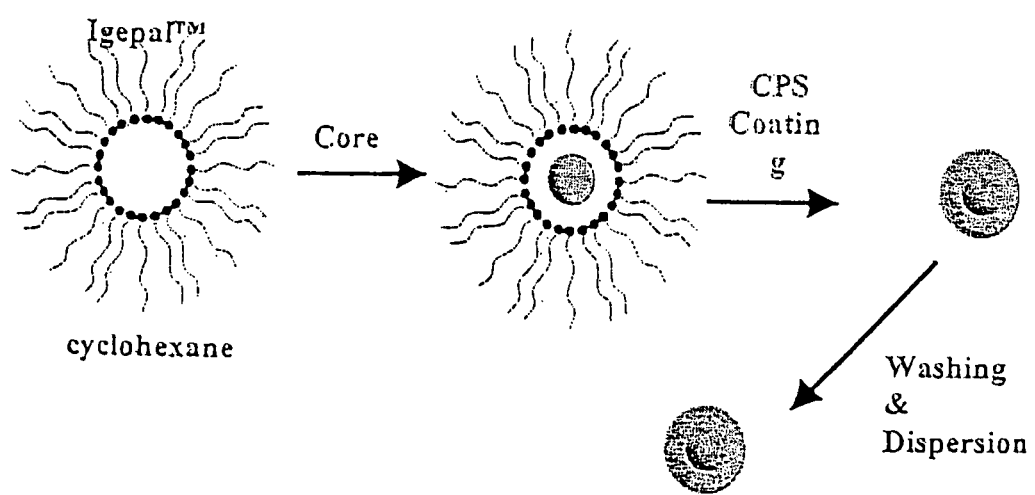
FIG. 1. Schematic of the preparation of the core-shell particles with a resorbable coating for drug delivery.

The present invention provides a method and system for maximizing and targeting the systemic delivery of growth-arresting pro-apoptotic, lipid-derived bioactive therapeutic compounds and/or hydrophobic chemotherapeutic agents and/or gene therapy agents to living cells of an animal or human in need of such therapy, utilizing nanoscale assembly systems, such as liposomes, resorbable and non-aggregating nanoparticles, metal or semiconductor nanoparticles or polymeric materials such as dendrimers or hydrogels, each of which exhibit improved lipid solubility, cell permeability, an increased circulation half life and pharmacokinetic profile having improved tumor or vascular targeting.

As used herein, "growth arresting" refers to living cells that are no longer responsive to growth factors or cytokines released from neighboring tissues. Moreover, "growth arrested" implies that the cells do not replicate their DNA and proliferate.

As used herein, pro-apoptotic refers to living cells or tumor tissues that undergo the process of programmed cell death.

As used herein, the phrase "lipid-derived" refers to substances that are the metabolites of natural lipids found in biological membranes.

As used herein, the term "bioactive" refers to agents that transduce information and initiate a signaling cascade from the plasma membrane of a cell to the nucleus where particular genes are either activated or inactivated resulting in a change to the phenotype of the cell (i.e., growth arrest and/or apoptosis).

As used herein, the terms "nanoscale" and "nanosize" refer to a special state of subdivision implying that a particle has an average dimension smaller than approximately 300 nm and exhibits properties not normally associated with the bulk phase, e.g., quantum optical effects.

As used herein, the phrase, "hydrophobic chemotherapeutic agents" refers to small molecules, peptides, proteins, peptidomimetics, and lipidomimetics that are used as drugs to diminish cell proliferation and/or to induce cell apoptosis and are relatively insoluble in aqueous environments.

As used herein, the terms "nanocomposite particles" and "nanoparticles" are interchangeable.

As used herein, the term "agglomeration" refers to the formation of an aggregate (a cohesive mass consisting of particulate subunits) in a suspension through physical (van der Waals or, hydrophobic) or electrostatic forces. The resulting structure is called an "agglomerate."

As used herein, non-aggregating is the state of "dispersed" bioparticulates.

In particular, the present invention provides a system and method for systemic, chronic or targeted delivery of a chemotherapeutic hydrophobic compound to an animal or a human in need of such therapy that includes a nanoscale assembly system and a growth-arresting, pro-apoptotic, lipid-derived bioactive compound or gene therapy agent. Nanoscale assembly systems can include, without limitation, liposomes, resorbable nanoparticles that can be encapsulated by a calcium phospho-silicate (CPS) shell, or polymeric materials, such as dendrimers or hydrogels, that can be formed to be both bioresponsive (bio-smart) and biodegradable.

The growth-arresting pro-apoptotic, lipid-derived bioactive compounds or gene therapy agents are delivered systemically via intravenous, catheter delivery, infusion pumps, micro-spheres, or salves for treating pathologies involving dysfunctional growth, such as cancer, neoplasm, arterial inflammatory disease, atherosclerosis, restenosis, vulnerable plaque or diabetes.

Examples of growth arresting pro-apoptotic, lipid-derived bioactive compounds include, without limitation, physiological ceramides and/or derivatives, cell-permeable ceramides and/or derivatives that have short-chain fatty acids at the SN-2 position, consisting of 2-10 carbon units, dimethyl sphingosine, trimethyl sphingosine, ether-linked diglycerides, ether-linked phosphatidic acids, sphingosines or sphinganines. Examples of gene therapy agents include, without limitation, oligonucleotides, ribozymes, DNA-zymes, plasmids, antisense or conventional Si-RNA or viral (AAV, AV or lenti) expressed SiRNA.

In one embodiment of the present invention, PEG-$C_8$ (750-5000 g/mol MW) and/or PEG-DSPE (2000-5000 g/mol MW) liposomes suitable for delivery of hydrophobic bioactive lipids, proteins and therapeutic agents, referred to herein as "pegylated" liposomals, are formulated having one or more membranes that are comprised of a growth-arresting lipid-derived bioactive compound or a gene therapy agent and/or cholesterol. Liposomes that are "pegylated," with PEG-$C_8$ (750-5000 g/mol MW) and PEG-DSPE (2000-5000 g/mol MW) also known as "stealth" liposomes, can be formulated that are capable of evading clearance from the circulation by the reticuloendothelial system (RES), and that can have binders attached thereto, such as antibodies or receptor ligands to target specific cells or tissues of the body. Liposomes, like other colloidal particles, are usually rapidly cleared from the circulation by the RES, primarily by Kupfer cells of the liver and fixed macrophages of the spleen. The rate of liposome uptake by the RES is believed to be related to the process of opsonization or dysopsonization of the liposomes. Liposomal therapeutic efficacy depends, therefore, on the ability to escape recognition by the RES and thus remain in the circulation for prolonged periods of time. The term "stealth" liposome, therefore, refers to this evasive property and is conferred on liposomes whose membranes contain bilayer-compatible species such as polyethylene glycol (PEG)-linked lipids. "Stealth" or pegylated liposomes thus have the potential to improve the hydrophilicity and bioavailability of drug releasing liposomes by evading the RES, and methods for liposome pegylation preparation have been known for many years, as reported by Blume, G. et al. (Biochem. Biophys. Acta, 1029:91-97, 1990). Moreover, targeting can be further achieved via the conjugation of particular targeting moieties, such as antibodies and/or receptor ligands, to PEG, which will promote the targeted accumulation into specific cells or tissues of the body. Alternatively, the embodiment may contain cationic lipids, such as dioleoyl-1,2-diacyl-3-trimethylammonium-propane, used for effectively delivering negatively charged oligonucleotides. In addition, "fusogenic" liposomes can be formulated where the entire membrane of the liposome fuses with the cell membrane of the target site to deliver the constituents and contents of the liposome therein. A fusogenic lipid is a destabilizing lipid that forms a hexagonal conformation in aqueous solution, thus generating inverse micelles that bind to cell membranes via an endocytotic or "fusogenic" process.

The liposomal vehicles of the present invention, therefore, ameliorates the primary problems associated with systemic delivery of lipid-derived bioactive compounds, such as $C_6$-ceramide, by preventing the bioactive lipid from precipitating out of solution so that it can be delivered to cells more effectively. Moreover, the present embodiment uses PEG-C8 to stabilize the lipid bilayer, allowing the liposome to contain concentrations of free bioactive $C_6$ ceramide of about at least 40 molar percent. In addition, the embodiment utilizes the PEG-C8 as an integral component of the liposome that contains the bioactive ceramide and/or a hydrophobic chemotherapeutic agent and/or a gene therapy agent. Moreover, PEG-C8 formulated liposomes ensures optimal intercalation and localization of the free ceramide into caveolin-rich lipid rafts, a prerequisite for membrane internalization and transfer to subcellular organelles, such as the mitochondria, for subsequent induction of apoptosis or programmed cell death of the targeted tissue or tumor.

Furthermore, the liposomes of the present invention can be applicable for both local and systemic delivery of therapeutic ceramide analogues. For instance, it has been demonstrated that the local and direct delivery of $C_6$-ceramide from ceramide-coated balloons of embolectomy catheters limits neointimal hyperplasia (restenosis) in rabbits after stretch injury. (Charles et al. Circ. Res. 2000 Aug. 18:87(4):282-8). Other groups have demonstrated that cell-permeable ceramide analogues in DMSO vehicle, delivered both intracistemally and intravenously, induces a neuroprotective effect in rats following focal cerebral ischemia. The clinical potential for the packaged delivery of $C_6$-ceramide with additional therapeutic agents in liposomal vesicles is significant. Studies have shown that ceramide may act synergistically with chemotherapeutic agents, such as paclitaxel and fenretinide. Thus, combined delivery of chemotherapeutic agents in $C_6$-formulated liposomes may further enhance apoptotic actions and at the same time diminish side effects by effectively lowering the concentration of each agent utilized in the liposomal formulation. Moreover, targeted immunoliposomes conjugated with tumor-specific antibodies or receptor ligands may also benefit from $C_6$-ceramide incorporation.

The mechanism of ceramide involvement in the apoptotic program is largely unknown, although ceramide accumulation appears to be associated with a number of apoptotic hallmarks, such as poly(A)DP-ribose polymerase (PARP) cleavage, DNA fragmentation, phosphatidylserine exposure and trypan blue uptake (Kolesnick, R. N. et al., Annu. Rev. Physiol., 60:643-665, 1998). Moreover, endogenous ceramide accumulates within mitochondrial membranes and, in part, induces cytochrome C release and resultant mitochondrial dysfunction and ultimately apoptosis. Ceramide can be generated through different metabolic routes in the cell. For example, it has been shown that there is a stress-induced metabolic conversion of sphingomyelin into ceramide by the enzyme sphingomyelinase in response to various treatments of cells, such as tumor necrosis factor-α(TNF-α), anti-Fas, serum withdrawal, and other agents. Additionally, ceramide can be generated through a de novo synthesis pathway, in which activation of serine palmitoyl transferase and/or ceramide synthase may play a pivotal role (Garzotto, M. et al., Cancer Res., 58:2260-2264, 1998). Exogenously added ceramides are generally able to mimic stress-induced apoptosis in a stereospecific manner, and inhibition of the formation of ceramide has been shown in some cases to inhibit progression of apoptosis (Wiesner, D. A. et al., J. Biol. Chem., 272:9868-9876, 1997). Exogenous ceramide intercalation and accumulation within caveolin-rich plasma membrane lipid rafts may facilitate internalization of these domains into subcellular organelles, including the mitochondria.

Apoptosis involves the orchestrated death of a cell and has been shown to be an important means by which organisms maintain homeostasis in proliferating tissues and systems, such as the immune system or in inflamed dysregulated cells or tissues as often observed in cancer, restenosis or atherosclerosis. (Frasca, L., et al., Crit. Rev. Immunol., 18:569-594, 1998). In fact, the loss of apoptosis control is a hallmark of carcinogenesis. Ceramide analogues have been shown to induce cellular apoptosis in tumorogenic cells in vitro. However, to date, there are no studies demonstrating the apoptotic and chemotherapeutic actions of ceramide in vivo, due to limited solubility upon systemic delivery. The term apoptosis often is used interchangeably with programmed cell death. It is distinguished from death by necrosis by the absence of an associated inflammatory response. Apoptosis is characterized by the occurrence of one or more cellular events that include loss of mitochondrial integrity, nuclear condensation, membrane blebbing, chromatin fragmentation or loss of membrane integrity resulting in phosphatidylserine exposure and trypan blue uptake (Wyllie, A. H., J. Cell Biol., 73:189-197, 1997). Biochemical mechanisms by which each of these cellular characteristics are regulated remain largely unknown. However, it is believed that the activation of a family of cysteine proteases known as caspases plays an important role in the progression of the apoptotic process (Thornberry, N. A. et al., Science, 281:1312-1316, 1998). Within this caspase family, initiator caspases are activated through an apoptotic stimulus and subsequently activate downstream effector caspases. These effector caspases in turn have a multitude of intracellular substrates, among which are components that are critically needed for cellular homeostasis. Cleavage of one or more of these substrates disregulates cell function and promotes specific morphological characteristics of the apoptotic program (Thornberry, N. A. et al., Science, 281:1312-1316, 1998). The mechanism by which PEG-C8 stabilizes liposomes to allow up to about 40 per cent molar ratios of free bioactive ceramide available for membrane intercalation and internalization and subsequent induction of apoptosis is a major embodiment of the invention. Modulation of apoptotic processes by compounds such as $C_6$-ceramide thus may offer valuable methods of treatment.

In a further embodiment of the present invention, growth-arresting lipid-derived bioactive compounds and/or gene therapy agents are loaded into resorbable nanoparticles for drug and gene therapy having a calcium phospho-silicate (CPS) shell and a drug core. The resorbable nanoparticles of the present invention can deliver the hydrophobic lipid or protein drugs or gene therapeutic agents systemically to living cells, which normally are not transportable through the circulation. The resorbable nanoparticles can have a diameter ranging from 1 to 300 nm, preferably less than 50 nm and most preferably 20 nm or less. Nanoparticles having a diameter of about 20 nm or less are able to cross the blood brain barrier (BBB), thus enabling the delivery of drugs directly into the central nervous system; a major advantage for treatment of carcinogenic brain or neural lesions. These nanosystems are also suitable for solid tumors, not limited to adenocarcinomas, melanomas, prostate, colon, lung (aerosol delivery) and breast tumors, as well as non-solid tumors such as leukemias The drug core either can be delivered as a solid or in an aqueous solution. A schematic for the preparation of the core-shell particles is shown in FIG. 1.

In particular, the method of synthesis for the resorbable nanoparticles includes a nonionic surfactant, such as poly (oxyethylene) nonylphenyl ether (IGEPAL™ 520 CO), or any other amphiphilic compound containing a polar head group and a non-polar tail, which is combined with water and a hydrophobic nonaqueous solvent, such as cyclohexane or iso-octanol in order to form a reverse micelle structure. Growth-arresting, pro-apoptotic, lipid-derived compounds or gene therapy agents can be suspended in the aqueous phase as a solution, suspension or micellular mixture of water and drug or water and gene therapeutic agent. The resulting reverse micelle containing the active agent within its core is coated with an inorganic resorbable coating which biodegrades in a physiological, i.e., isotonic, environment. CPS is an example of a resorbable coating, having the following composition: $Ca_x(PO_4)_y zSiO_2$, where $0.1 \leq x \leq 10$ $0.1$, $0.1 \leq y \leq 10$, and $0 \leq z \leq 10$. The composition can be adjusted to provide different rates of resorption of the shell in physiological environments, with higher silica and lower calcium and phosphate concentrations resulting in a slower resorption rate.

A key feature of the synthesis of the resorbable nanoparticles is the proper dispersion of the nanoparticles in a liquid medium. Suitable liquids can include, without limitation, deionized water, saline solution, water-ethanol mixtures or other liquid-suspending media suitable for a physiological environment and/or any additional processing steps, e.g., granulation processes such as spray-drying prior to tablet formulation for oral delivery. This is accomplished first by washing the nanoparticles in order to remove excess amphiphilic compound and any other ions or additives to ensure that optimal dispersion of the nanoparticles is achieved. Additionally, it is necessary to concentrate the suspension during washing to produce a suspension at a high enough concentration in order to deliver the drug or gene therapy agent at a sufficient dosage. This is achieved using size exclusion high performance liquid chromatography (SEC) modified specifically for the silicate-containing shell nanoparticles. Such modifications are necessary to prevent solid bridge formation between the contacting nanoparticles that results in persistant agglomeration. The size of the primary nanoparticles produced according to the method of the present invention can range between about 1.0 to 300 nm. This procedure prevents agglomeration of the nanoparticles, which can be well over 1 micron, as measured by particle size distribution measurement techniques, such as quasi-elastic light scattering or centrifugation or sedimentation with optical density determination. Thus, nanoparticle suspensions that are not processed as described herein can result in significantly altered flow units due to the agglomeration during the washing and recovery steps than what would be the case for primary size nanoparticles.

The critical modifications of the SEC collection and washing steps of the nanoparticles includes using shorter elution columns that contain microporous silica particles having a diameter of about 20 microns, as well as chemical modifications. Chemical modifications include, without limitation, adding ethanol or any other suitable alcohol to the reverse micelle suspension after synthesis of the nanoparticles to produce a homogeneous nanoparticle suspension. The substitution of alcohol in place of the typical use of water or acetone prevents the formation of agglomerated masses of nanoparticles having flow units much greater than primary nanoparticle size flow units. Another critically important chemical modification is the attachment of an organic or inorganic dispersant which acts on the surface of the nanoparticles to provide an electrosteric layer that prevents the nanoparticles from persistent agglomeration. Suitable organic dispersants include, without limitation, citric acid, tartaric acid or acetic acid. Suitable metal-organic dispersants include, without limitation, alkylamine silane coupling agents, such as aminopropyltrichlorosilane; 3-aminopropyl-trimethoxysilane (APS); 3-aminopropylsilsesquioxane); 3-glycidoxypropyl-trimethoxysilane (GPS); trimethoxysi-lyl-propyldiethylenetriamine (DETA); 3-trimethoxysilypropylsuccinic anhydride; and alkylcarboxylic acid silane coupling agents, such as amide-linked carboxyl groups. Suitable ionic dispersants include, without limitation, excess calcium, phosphate or pyrophosphate.

Furthermore, it is necessary that the microporous silica particles that are used to pack the SEC column be surface-treated with the identical dispersing agent in order to produce an electrosteric barrier that prevents the nanoparticles from adhering to the microporous silica surfaces during passage through the column. It also is necessary to control pH levels during the SEC nanoparticle concentration and washing steps. Thus, acids, such as, without limitation, nitric acid, acetic acid or hydrochloric acid; or bases such as, without limitation, sodium hydroxide or potassium hydroxide, are added as needed in order to maintain pH levels within a range of between about 6 and 8. With a pH greater than 8, the charge on the surface of the nanoparticles is too low and agglomeration results. With a pH less than 6, the concentration of acid or base is too high and the resultant ionic strength can cause agglomeration during the washing step. Ceramides and other lipid-derived bioactive mediators are resistant to all of these acidic or alkaline procedures.

Additionally, a carbodiimide-mediated polyethylene glycol (PEG) coupling agent can be attached to the alkylamine silane or alkylcarboxylic acid coupling agent to further ensure the dispersed state of the nanoparticles in vivo and to provide an attachment point for binders, such as antibodies or ligands for expressed receptors, onto the PEG coupling agent, thus enabling intracellular drug delivery of the ceramide enriched or encapsulated nanoparticles to targeting tumor specific sites.

In another embodiment of the present invention, the nanoscale assembly system is comprised of polymeric material, such as dendrimers or hydrogels, which are loaded with growth-arresting, pro-apoptotic, lipid-derived bioactive compounds and/or gene therapy agents. The dendrimers or hydrogels are individual polymers that are combined to form materials that are both bio-smart, i.e. respond to stimuli, and biodegradable in vivo. It was discovered, after investigation and experimentation, that materials which combine a smart segment with a degradable hydrophobic and/or hydrophilic segment can be used for drug delivery. A segment is considered to be a covalently bound portion of the material and can have a plurality of polymerized units. For example, a segment can include several polymerized monomer units up to about several thousand polymerized monomer units. These segments can have any length and any molecular weight, however it is preferred that each segment has a molecular weight that is roughly large enough to approximate a desired property expected for that polymer segment.

The polymeric material when used alone is limited by sub-optimal or non-biodegradability. Thus, combining a smart polymer segment with a biodegradable polymer segment results in a material considerably more versatile than the individual materials. By combining both bioresponsive and biodegradable polymers, a drug delivery system is fashioned which is both biodegradable and responsive to physiological stimuli. In particular, a multifunctional polymeric material is provided comprising a smart segment and a biodegradable segment, wherein the biodegradable segment includes a hydrophobic segment (suitable for binding or interacting with a chemotherapeutic agent) and a hydrophilic segment.

A number of natural and synthetic biodegradable polymers are known. Some have been studied, including polyesters, such as polylactides (PLA), poly(L-lactic acid), poly(D,L-lactic acid), poly(lactide-co-glycolides) (PLGA), biotinylated poly(ethylene glycol-block-lactic acid), poly(alkylcyanoacrylates) and poly(epsilon-caprolactone); polyanhydrides, such as poly(bis(p-carboxyphenoxy) propane-sebacic acid) (PCPP-SA), polyorthoesters, polyphosphoesters, polyphosphazenes, polyurethanes, and poly (amino acids), polysaccharides, such as dextran, in the forms of microcapsules, microparticles, nanoparticles, hydrogels and micelles. All such biodegradable polymers are contemplated in the present invention as segments of a multifunctional material.

The forgoing polymers degrade by hydrolytic or enzymatic cleavage of the backbone and, hence, are non-toxic and non-inflammatory after drug depletion. The degradation properties of the polymers depend on their chemical composition, tacticity, crystallinity, molar mass, morphology, size and shape, and also pH and temperature. The chemical and physical properties of biodegradable polymers are known to influence the drug release patterns, and the release kinetics of the loaded drugs are controlled by both drug diffusion and polymer degradation.

Another approach to affect the degradation rates of dendrimers or hydrogels include coating or grafting hydrophobic materials, e.g. PLA and PLGA micro/nanoparticles, with poly-L-lysine (PLL) due to the PLL's charge, hydrophilicity and targeting capability. For example, it has been shown that microparticles composed of poly(L-lactic acid-co-L-lysine) grafted with PLL have significantly increased release rates of rhodamine B compared to those without the PLL side chains. Furthermore, PLGA grafted with PLL micelles display 10 times higher transfection efficiency and 5 times less cytotoxicity than PLL. The present invention contemplates the use of such coating and grafting techniques in providing hydrophilic-hydrophobic degradable segments.

Dendrimers are defined by regular, highly branched segments leading to a relatively monodisperse, tree-like or generational structure. Dendrimers possess three distinguishing architectural features: the core; the interior area containing branch upon branch of repeat units or generations with radial connectivity to the core; and an exterior or surface region of terminal moieties attached to the outermost generation. A dendrimer can be defined into a multitude of structures by tuning these three architectural components. Dendrimers that are highly branched and reactive three-dimensional macromolecules have become increasingly important in biomedical applications due to their high degree of molecular uniformity, narrow molecular weight distribution, specific size and intriguing structural properties such as internal voids and cavities, and a highly functional terminal surface. The spatially arranged functional groups can react with a variety of molecules, for example, hydrophilic molecules such as PEO (polyethylene oxide or PEG) to increase their blood circulation times, contrast agents for use in magnetic resonance imaging (MRI), and targeting molecules to localize to desired tissue sites.

Currently available dendrimers contain benzyl ether, propyleneimine, amidoamine, L-lysine, ester and carbosilane dendritic segments. Among them, cationic polyamidoamine (PAMAM) dendrimers have been widely studied and were reported to mediate high levels of gene transfection in a wide variety of cells, depending on the dendrimer-DNA ratio, the size and especially the flexibility of the dendrimers. PAMAM dendrimers are considered targeted delivery systems, and can enhance accumulation within certain tumor microvasculature, increase extravasation into tumor tissue. Poly(L-lysine) (PLL) dendrimer is another polycationic dendrimer containing a large number of surface amines and considered to be capable of the electrostatic interaction with polyanions, such as nucleic acids, proteoglycans found in extracellular matrix and phospholipids of the cell membrane. These polymers can localize drugs, including lipid-derived bioactive growth arresting, pro-apoptotic metabolites or agents to the targeted membranes.

However, polycationic dendrimers still have in vivo toxicity problems and are resistant to degradation in the body and are thus less suitable for drug delivery. To improve the cytotoxicity of PAMAM dendrimers, the cationic amine terminal groups of the dendrimers can be replaced with anionic carboxylate terminal groups. The present inventive materials address some of the disadvantages of dendrimer structures prepared from individual components by combining smart and degradable segments as arms, branches, or dendrons of a dendrimeric structure. Such dendrimeric materials can be prepared by coupling a thermoresponsive polymer segment with a biodegradable polymer segment in a chemical bond forming reaction.

Dendrimers also can be prepared as nano-sized particles. It is believed that particles having a size of about 1 nm to 1000 nm hold a significant advantage in transporting and targeting drugs to inflamed, proliferative or transformed tissues. Drugs are loaded into the nano-sized dendrimers by adsorption, entrapment and covalent attachment, and released from the nano-sized dendrimers by desorption, diffusion, polymer erosion or some combination of any or all the above mechanisms. In vitro and in vivo experiments show that nano-sized dendrimers can have long blood circulation times and a low RES uptake when they are stabilized by dextran and coated with polysorbate 80. The nano-sized dendrimers may be able to interact with the blood vessel or solid tumor cells, and then be taken up by these cells by endocytosis. Dendrimers are believed, therefore, to have a great potency to deliver drugs to tumorigenic or inflamed/proliferative tissues due to increased circulatory half-life.

Recent advances in nanotechnology offer enormous potential for controlled delivery and targeted release of hydrophobic therapeutics. The nanoscale dendrimeric assembly system of the present invention is both responsive to temperature stimuli and hydrolytically biodegradable, allowing for the targeted and sustained delivery of $C_6$ to solid tumors. It has been demonstrated that $C_6$ can be loaded into temperature-sensitive, "smart" dendrimers, and that this drug-polymer complex can effectively inhibit the proliferation, as well as induce apoptosis, of MDA estrogen-negative breast cancer cells. The application of acute local hyperthermia, via a heat pack, infrared or ultrasound, to the area of a solid tumor will trigger the release of $C_6$ into diseased tissue. Thus, thermoresponsive nanoscale dendrimers can serve as an optimal solution for targeted and controlled delivery of therapeutic agents, including ceramide, to solid tumor tissue, a concept coined as "physiological hyperthermic drug delivery."

Dendrimers in Drug Delivery.

Liposomal drug delivery technology is slowly being eclipsed by more advanced drug delivery systems that incorporate polymer chemistry technology in order to engineer stable nanoparticles with a dynamic array of drug delivery advantages. For instance, polymeric nanoparticles are capable of prolonged bioavailability, diseased cell targeting, and bioresponsive and controlled drug release (17). Drugs are loaded into the polymeric nanoparticles by adsorption, entrapment and covalent attachment, and released from the nanoparticles by desorption, diffusion, polymer erosion or some combination of any or all mechanisms. Dendrimers, highly branched and reactive three-dimensional nanoparticles, are suitable for biomedical applications due to their high degree of molecular uniformity, narrow molecular weight distribution, specific size and intriguing structural properties such as internal voids and cavities, and a highly functional terminal surface. The dendrimers of the present invention are comprised of a polycationic polymer (poly(L-lysine), PLL), a biodegradable polymer (poly(L-lactic acid), PLLA), and a thermo-responsive polymer (poly(N-isopropylacrylamide), PNIPAAM). Hydrophobic agents, such as $C_6$, are loaded into the dendrimer in concentrations up to 1000 mg/ml, by hydrophobic-hydrophobic interactions with the PLLA. Incorporation of responsive polymers with biodegradable polymers has advantages in achieving sustained release of drugs in response to a physiological stimuli, such as temperature.

Smart or responsive polymers are responsive to physical, chemical, or biological stimuli, such as temperature, solvent composition, pH, ionic strength, pressure, electric field, light and metabolites. Among thermo-responsive polymers, poly(N-isopropylacrylamide) (PNIPAAM) has been extensively used for controlled drug delivery, since it exhibits a unique solubility transition at the lower critical solution temperature (LCST) in an aqueous solution in the vicinity of 32° C. It expands and swells when cooled below the LCST, and it shrinks and collapses when heated above the LCST. The LCST of PNIPAAM can be manipulated for controlling the loading and the release of drugs by incorporating hydrophobic and hydrophilic units, and crosslinkers into PNIPAAM.

Importantly, PNIPAAM-based polymers can be used as reversible targeting moieties for site-specific drug delivery. In the present invention, the polymers are designed with the LCST between 37° C. and 42° C. At a body temperature of 37° C., below the LCST, the polymers are soluble in the physiological fluids, evade the body's reticulo-endothelial system (RES) and increase the loaded drugs' blood circulation time. When the temperature is increased to 42° C. via, without limitation, local ultrasound, infrared and/or heat patches, which is a temperature higher than the LCST of polymers at the targeting site, the polymers accumulate at the targeting site and release therapeutic drugs with high local concentrations. It has been shown that systemic injection of poly(NIPAAM-co-acrylamide) with a LCST of 40° C. in mice accumulated the copolymer at solid tumors by local hyperthermia at a 2 fold greater degree than that for heated and unheated control groups. Additionally, biodegradable and thermoresponsive micelles composed of poly(N-isopropylacrylamide-co-N,N-dimethylacrylamide)-b-poly(D,L-lactide) have been prepared with a LCST of 40° C. It has been shown that the cytotoxicity of the anticancer drug adriamycin loaded in the micelles against bovine aorta endothelial cells was higher than that of free adriamycin above the LCST at 42.5° C. due to accelerated uptake of the micelles by the cells. The dendritic nanoparticles of the present invention expand upon the thermo-responsive properties of PNIPAAM, as the polymer is covalently linked to polycationic PLL (hydrophilicity and stability) and biodegradable PLLA (hydrophobic, controlled-release). Moreover, this multi-functional dendrimer can be loaded with the pro-apoptotic lipid $C_6$ to induce breast cancer cell apoptosis.

Hydrogels are three-dimensional crosslinked polymer networks that swell in an aqueous environment by absorbing large amounts of water while maintaining their structure. Due to their high water content, biocompatibility, and unique mechanical properties, hydrogels have attracted wide interests in biomedical applications such as drug delivery and tissue engineering. The environmentally-sensitive hydrogels of the present invention can control drug release by changing their structures in response to environmental stimuli, such as temperature, pH, electrical signal, ionic strength, etc. Covalently and non-covalently (physically) crosslinked temperature-sensitive, biodegradable gels are preferred materials as hydrogels.

In particular, hydrogels are prepared as copolymeric networks composed of N-isopropylacrylamide (NIPAAM) or a derivative thereof as a smart or responsive component; poly (L-lactic acid) (PLLA) or a derivative thereof as a hydrolytically degradable and hydrophobic component; and dextran or a derivative thereof as an enzymatically degradable and hydrophilic component. The components or segments can be of any length including from about 3 monomer units to about 10,000 monomer units, e.g. about 3 to 5,000 units. The material or segments can further comprise other monomer units to adjust the materials properties. For example, the hydrogel can also include anionic (acrylic acid) and cationic (acrylic amine) units for increasing pH and ionic strength sensitivity of the gel.

PNIPAAM-PLLA-dextran hydrogels are thermo-responsive showing a lower critical solution temperature (LCST) at approximately 32° C., and their swelling properties strongly depend on temperature changes, the balance of the hydrophilic/hydrophobic components and the degradation of the PLLA component. The degradation of the hydrogels caused by hydrolytic cleavage of ester bonds in PLLA component, is faster at 25° C., below the LCST than at 37° C., above the LCST, as determined by ATR-FTIR and weight loss measurement.

It is stated, without being bound by the theory, that when therapeutic compounds, such as growth-arresting, pro-apoptotic, lipid-derived bioactive compounds and/or gene therapy agents, are incorporated into nanoscale assembly systems, such as liposomes, resorbable, non-aggregating nanoparticles, or polymeric materials, such as dendrimers or hydrogels, their systemic delivery to cancerous cells is augmented, thus enhancing greatly the potency of the growth-arresting, pre-apoptotic compounds. Additionally, ceramide-enriched or encapsulated nanotechnology can be engineered to deliver lower doses of other hydrophobic chemotherapeutic agents or gene therapies in a combination therapy to achieve higher efficacy with diminished side effects.

The following examples are intended to further illustrate certain preferred embodiments of the invention and are not limiting in nature. Those skilled in the art will recognize, or be able to ascertain, using no more than routine experimentation, numerous equivalents to the specific substances and procedures described herein.

EXAMPLE 1

$C_6$-Ceramide-induced Apoptosis of Breast Cancer Cells via Liposomal Delivery

Materials and Cell Culture

Egg phosphatidylcholine (EPC), dioleoyl phosphatidylethanolamine (DOPE), dioleoyl phosphatidylcholine (DOPC), cholesterol (CH), polyethyleneglycol (2000-5000)-distearoyl phosphatidylethanolamine (PEG-DSPE), D-erythro-hexanoyl-sphingosine ($C_6$-ceramide), polyethyleneglycol-750-$C_8$-ceramide (PEG-C8), dioleoyl-1,2-diacyl-3-trimethyl-ammonium-propane (DOTAP) were purchased from Avanti Polar Lipids (Alabaster, Ala.). Di-hydro-erythro hexanoyl-sphingosine ($DHC_6$) was purchased from Biomol (Plymouth Meeting, Pa.). [$^3$H]-$C_6$ was obtained from ARC (St. Louis, Mo.), [$^3$H]-thymidine was purchased from ICN (Costa Mesa, Calif.) and cholesteryl-1,2-$^3$H(N) hexadecyl ether ([$^3$H]-CHE) was obtained from PerkinElmer (Boston, Mass.). Silica gel 60 thin layer chromatography plates were purchased from EMD Chemicals (Gibbstown, N.J.). Formvar/carbon-coated 400 mesh copper grids were purchased from Electron Microscopy Sciences (Fort Washington, Pa.), and poly-L-lysine was obtained from Sigma (St Louis, Mo.).

Antibodies specific for phosphorylated-Akt (pAkt) and Akt-1,2,3 were purchased from Cell Signaling (Beverly, Mass.). Insulin-like Growth Factor-1 (IGF-1) was obtained from CalBiochem (San Diego, Calif.). For Western blotting, 4%-12% pre-casted SDS-PAGE gradient gels were obtained from Invitrogen (Carlsbad, Calif.) and ECL reagent from Amersham (Piscataway, N.J.). The TUNEL Apoptosis Detection Kit was obtained from UpState Biotechnology (Waltham, Mass.). The Vybrant Apoptosis Assay Kit #3 was purchased from Molecular Probes (Eugene, Oreg.), and the Apo-ONE Homogeneous Caspase-3/7 Assay was obtained from Promega (Madison, Wis.). RNAse was purchased from Roche (Indianapolis, Ind.) and propidium iodide (PI) from Sigma (St. Louis, Mo.). Human MDA-MB-231 (MDA) breast adenocarcinoma cells were obtained from ATCC (Manassas, Va.) and grown at 37° C. in RPMI 1640 supplemented with 10% FBS. This cell line is a highly aggressive metastatic, estrogen receptor-negative, model of human breast cancer.

Liposome Formulation and Extrusion

Lipids were formulated and tested for their ability to incorporate C6 into liposomal drug delivery vesicles. Briefly, lipids, dissolved in chloroform (CHCl3), were combined in specific molar ratios, dried under a stream of nitrogen above lipid transition temperatures, and hydrated with sterile phosphate-buffered saline (PBS). The resulting solution underwent sonication for 2 min followed by extrusion through 100 nm polycarbonate membranes. Incorporation efficiency was determined by incorporating trace amounts of [3H]C6 in the formulation, extracting constituent lipids in CHCl3/MeOH (2:1), and comparing radioactivity before and after extrusion using a scintillation counter. Formulations for in vivo administration comprised of DSPC:DOPE:DSPE-PEG(5000):C8-Ceramide-PEG(750):C6-Ceramide (3.75:1.75:0.75:0.75:3.0, molar ratios). The addition of PEG (750)-$C_8$ allows for up to 40 molar percent $C_6$-ceramide. The bioactivity of these pegylated formulations were confirmed in 410.4 mammary adenocarcinoma cells. The composition of formulated liposomes was validated by extracting constituent lipids in chloroform/methanol (2:1), followed by resolution on preheated silica gel 60 thin layer chromatography (TLC) plates using a CHCl3/MeOH/ddH2O (60:25:4) solvent system. Lipids were visualized in an iodine chamber. Transmission electron microscopy (TEM) was utilized to characterize the size and morphology of the formulated liposomes.

Transmission Electron Microscopy (TEM)

In order to characterize the size and morphology of the formulated liposomes, TEM was utilized. Initially, formvar carbon-coated 400 mesh copper grids were coated with poly-L-lysine for 10 minutes, in order to promote vesicular binding to the hydrophobic grids. Liposomal samples were next applied to the dried grids and allowed to adhere for 5 minutes. Negative staining was performed by applying 1% phosphotungstic acid (pH 7.0) to the dried grid for an additional 5 minutes. The sample was observed at 21,500× magnification with an accelerating voltage of 60 kV.

TEM analysis confirmed that C6-incorporated liposomal vehicles were produced with a homogeneous size distribution between 85 and 140 nm in diameter for all formulations (FIG. 2A). FIG. 2B illustrates the average size of the liposomal formulations. With the incorporation of trace amounts of [3H]C6 into conventional formulations, we observed that there was no significant loss of ceramide during the extrusion process (FIG. 2C). Additionally, lipid extracts from conventional liposomes were run on TLC plates, confirming that there was no visual diminution of lipid constituents during the extrusion process (FIG. 2D).

In Vitro Pharmacokinetics

Trace amounts of $[^3H]C_6$ were incorporated into liposomal formulations to quantify the amount of liposomal delivery compared to nonliposomal administration. Human MDA-MB-231 (MDA) breast adenocarcinoma cells were seeded at $3.5 \times 10^4$ cells/well in 24-well plates and grown overnight in media containing 10% FBS. Cells were then treated with liposomal or nonliposomal $C_6$ containing trace amounts of either $[^3H]C_6$ or $[^3H]CHE$ in media supplemented with 1% FBS for various time intervals. Liposomal $C_6$ was added directly to cell media, and nonliposomal $C_6$ was added in dimethylsulfoxide (DMSO) vehicle to a final concentration of ≤0.1% (v/v). At the indicated time points, the media was removed, and cells were washed once with cold PBS to dissociate liposome/membrane-nonspecific interactions. The cells were then solubilized with 1% SDS, and either $[^3H]C_6$ or $[^3H]CHE$ accumulation into MDA cells was assessed with a scintillation counter.

Figure 3A:
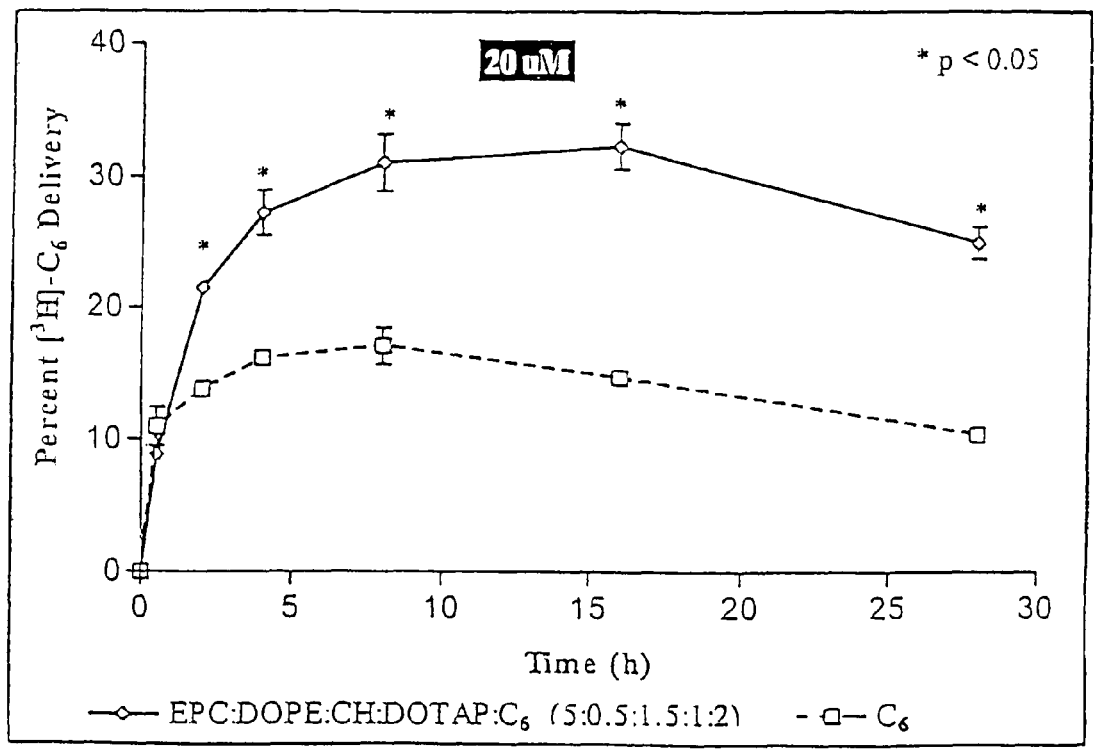
FIG. 3A. In vitro pharmacokinetics of $C_6$ delivery. Liposomal delivery of $C_6$ resulted in a greater cellular accumulation of $C_6$ as a function of time than nonliposomal delivery. (A) Liposomes were formulated with trace amounts of [$^3$H] $C_6$ to determine the kinetics of ceramide delivery to MDA cells. The total counts of liposomal and nonliposomal $C_6$ added to the cells was set at 100%. At 20 μM, $C_6$ accumulation peaks at approximately 16 h. Mean±S.E., n=3 separate experiments. *, p<0.05 when comparing liposomal $C_6$ accumulation with nonliposomal $C_6$ accumulation.

Results showed that liposomal formulations delivered $C_6$ more effectively and efficiently than nonliposomal administration of $C_6$ in the presence of 1% FBS (FIG. 3A). Cationic liposomal delivery resulted in a 2-fold increase in ceramide accumulation by MDA cells, with a maximal accumulation observed at approximately 16 h. Conventional and pegylated liposomes were observed to have similar in vitro pharmacokinetic profiles.

The mechanism by which $C_6$ is released or transferred from liposomal vehicles into cellular membranes then was investigated. Using a nontransferable cholesterol lipid marker, $[^3H]CHE$, as a probe for liposome/cell membrane association, liposomes were tagged with either $[^3H]C_6$ or $[^3H]CHE$ and incubated with MDA cells for the indicated time periods. As shown in FIG. 3B, liposomes mediated the transfer of $C_6$, but not cholesterol, from drug vehicle to cellular membrane. Furthermore, as $C_6$ accumulation increased over time, CHE accumulation failed to significantly increase above background levels. The disparity between ceramide and cholesterol accumulation also is observed in a dose-dependent manner (FIG. 3C). This suggests that $C_6$ is delivered via lipid transfer processes that permit $C_6$ to partition out of the liposomal layer into the plasma membrane bilayer without associated liposome/cell membrane fusion.

[3H]-Thymidine Cell Proliferation

To determine the utility of conventional lipid formulations for the delivery of short-chain ceramide to MDA cells, a [3H]thymidine proliferation assay was performed. Briefly, MDA cells were seeded at $3.5 \times 10^4$ cells/well in 24-well plates and grown overnight prior to 24 h of serum starvation. At hour 12 of serum starvation, cells were treated with liposomal or nonliposomal $C_6$ for the remainder of serum starvation. Following serum starvation, media was then supplemented with FBS (10% final concentration) for an additional 12 h, and cellular proliferation was assayed with the addition of 0.5 mCi/ml [3H]thymidine for the final 4 h of treatment. Cells were washed once with cold PBS and then twice with 10% trichloric acetic acid for 10 min. Cells were solubilized with 0.3 N NaOH, and [3H]thymidine incorporation into acid-insoluble DNA was assessed with a scintillation counter.

As shown in FIG. 4A, a conventional liposome containing egg phosphatidylcholine (EPC) and cholesterol (CH) (solid lines) supplemented with $C_6$ displayed a significant dose-dependent inhibition of MDA cell proliferation. The addition of a vesicle-destabilizing lipid, dioleoyl phosphatidylethanolamine (DOPE), into a conventional formulation also enhanced the bioactivity of $C_6$. MDA cells, in the presence of 10% FBS for 12 h of treatment, were completely growth-inhibited when treated with liposomal $C_6$ at 25 μM or greater. The delivery of $C_6$ in liposomal formulations reduced the IC50 approximately 3-fold, decreasing from 15 to 5 μM, nonliposomal to liposomal, respectively. These conventional formulations displayed an improved dose-response inhibition of growth in MDA cells compared with nonliposomal administration of $C_6$ in DMSO vehicle (dashed line, open circle), indicating improved potency and efficacy. Liposomes without $C_6$ (Ghost; dashed line, open square) as well as PBS controls did not display significant growth inhibition, implicating $C_6$ as the only bioactive agent. This study demonstrated that that $C_6$-formulated conventional liposomes were more effective as an antiproliferative than freely administered $C_6$.

$C_6$-incorporation into cationic lipid formulations next were investigated (FIG. 4B). Even though Ghost cationic liposomes (dashed line, open triangles) formulated with a positively charged lipid, dioleoyl-1,2-diacyl-3-trimethylammonium-propane (DOTAP), enhanced MDA cell proliferation alone, $C_6$-incorporated cationic liposomes (solid line, open triangle) dose-dependently reduced MDA cell proliferation. This cationic formulation was more effective than nonliposomal $C_6$ administration (dashed line, open circle) but not as effective as a conventional formulation (solid line, open square). This indicates that cationic liposome formulations could also be used to deliver bioactive ceramide to dose-dependently inhibit cell proliferation.

The role of pegylated lipid to further enhance the bioactivity of $C_6$ next was investigated. $C_8$-ceramide (PEG-C8) was chosen because of its additional potential benefit to promote liposome/membrane fusion. Additionally, the inclusion of PEG-C8 is known to facilitate time-release properties of liposomal bilayers, with the added benefit of bioavailability extension. Moreover, the present embodiment uses PEG C8 to stabilize the lipid bilayer, allowing the liposome to contain concentrations of free bioactive $C_6$ ceramide up to at least 30 molar percent. In addition, the embodiment utilizes the PEG C8 as an integral component of the liposome that contains the bioactive ceramide and/or a hydrophobic chemotherapeutic agent and/or a gene therapy agent. Moreover, PEG-C8 formulated liposomes ensures optimal intercalation and localization of the free ceramide into caveolin-rich lipid rafts, a pre-requisite for membrane internalization and transfer to subcellular organelles including the mitochondria for subsequent induction of apoptosis or programmed cell death of the targeted tissue or tumor.

Figure 4C:
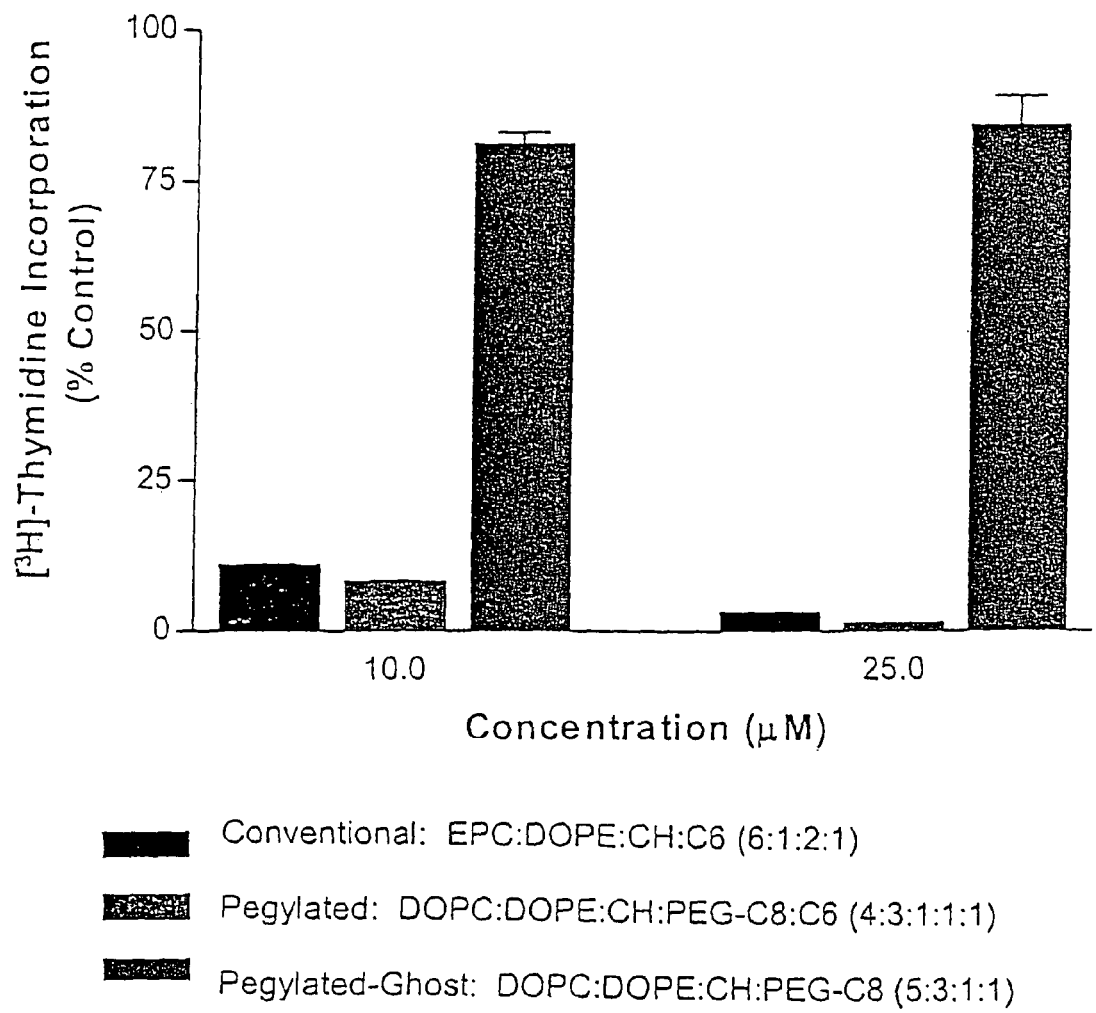
FIG. 4C. Thymidine incorporation growth assay showing that pegylated liposome $C_6$ delivery is more potent than non-liposomal $C_6$ in estrogen receptor-negative MDA breast cancer cells.

Pegylated liposomes did not markedly effect MDA cell proliferation, demonstrating that PEG-C8 is biochemically inert. However, $C_6$-incorporated pegylated liposomes were as if not more, effective at inhibiting proliferation as conventional liposomes at 10 and 25 µM (FIG. 4C). This indicated that a pegylated liposomal formulation designed for systemic drug delivery also is an effective vehicle for $C_6$-mediated inhibition of MDA cell proliferation. Taken together, $C_6$ delivered in multiple liposomal formulations displays an improved dose-response inhibition of growth compared with nonliposomal $C_6$, indicating improved potency and efficacy.

MTS Cytotoxicity Assay

Figure 5:
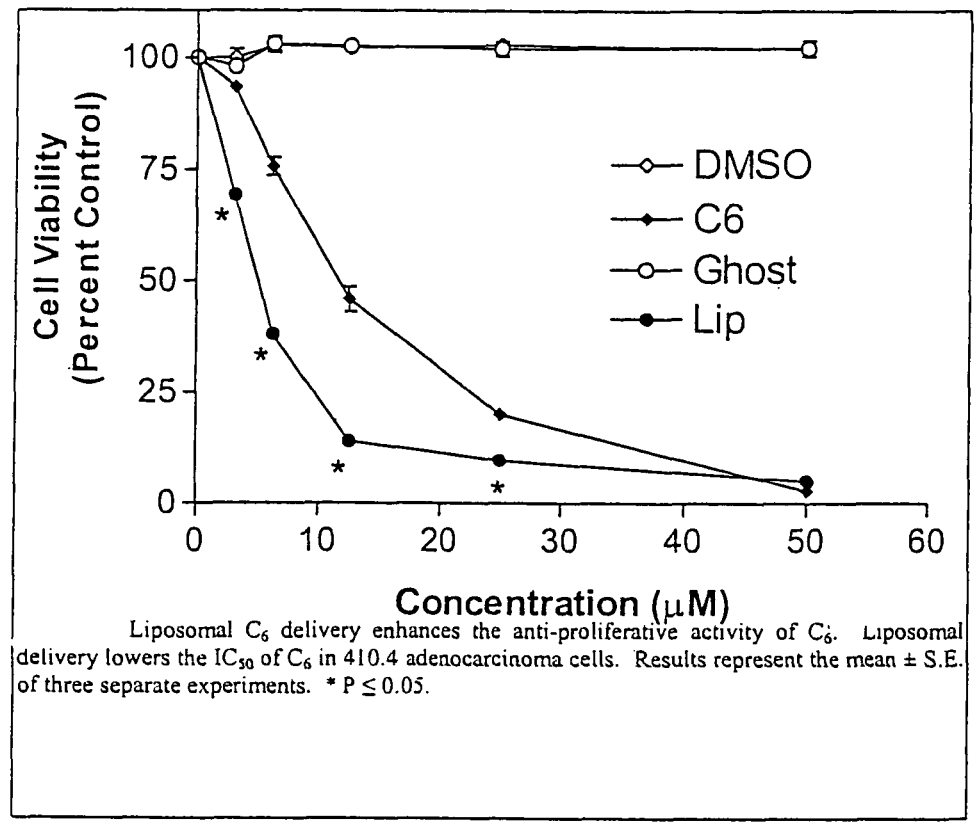
FIG. 5. Pegylated liposomal C6 [DSPC/DOPE/DSPC-PEG(5000)/$C_8$-PEG(750)/$C_6$-Cer (3.75:1.75:0.75:0.75:3.0)] delivery enhances the anti-proliferative activity of C6. Liposomal delivery lowers the IC50 of C6 in 410.4 adenocarcinoma cells. The incorporation of PEG-$C_8$ to 0.75 allows for the incorporation of 30 mole percent $C_6$. Results represent the mean±S.E. of three separate experiments. *p<0.05.

To assess the in vitro efficacy of pegylated formulations used for in vivo studies, we tested the formulations on murine 410.4 mammary adenocarcinoma cells. The 410.4 cells were plated in 96-well plates and treated with pegylated liposomal or free C6 for 24 hours in culture media supplemented with FBS to 1%. Cytotoxicity was assessed using the Promega Cell Titer Proliferation Kit (Promega) according to the manufacturers instructions. Pegulated liposomal-$C_6$ delivery results in enhanced cellular toxicity. The administration of liposomal-C6 formulations lowers the IC50 of C6, compared to free administration of C6 in DMSO vehicle (FIG. 5). These data indicate a 35-40% reduction in the $IC_{50}$ of $C_6$-ceramide when delivered in PEG-$C_8$ liposomal formulations. Treatments were performed in the presence of 1% FBS for 24 hours.

Caspase Assay

Figure 6:
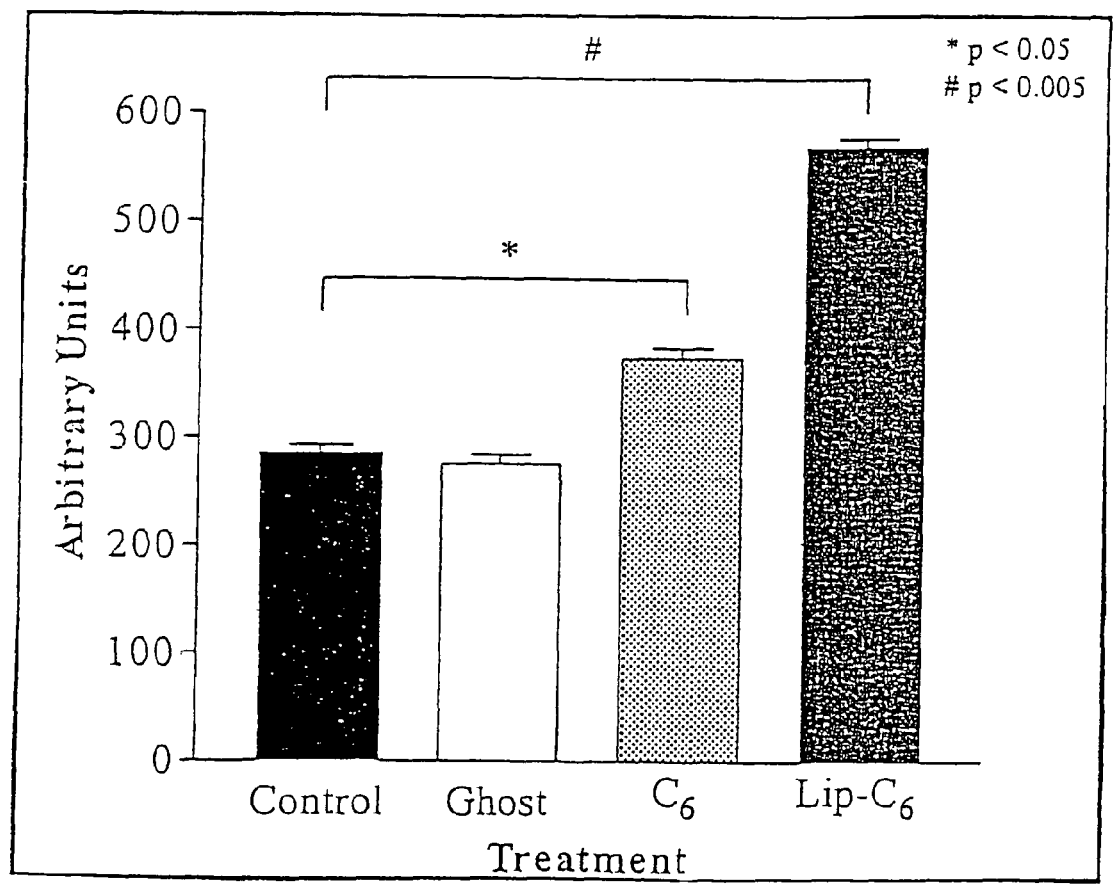
FIG. 6. As a measure of apoptosis, liposomal C6 delivery augments caspase-3/7 activity in MDA cells.

Apoptosis is associated with the up-regulation of caspase activity, thus caspase-3/7 activity following treatment of MDA cells with pegylated liposomes was assessed. Briefly, MDA cells were seeded to a density of $6.0 \times 10^3$ cells/well in 96-well plates and grown for 48 h in culture media containing 10% FBS. Cells were then treated with liposomal or nonliposomal $C_6$ for 24 h in media containing 1% FBS. Caspase-3/7 enzymatic activity levels were measured using the Apo-ONE homogeneous caspase-3/7 assay (Promega, Madison, Wis.) according to standard protocol known in the art The results showed that MDA cells treated with pegylated liposomal ceramide displayed significantly greater caspase-3/7 activity than cells treated with nonliposomal ceramide (FIG. 6). No significant change in caspase-3/7 activity was observed with Ghost treatments. Taken together, these results indicate that $C_6$-formulated liposomes were more effective than nonliposomal administration of $C_6$, resulting in significant inhibition of MDA cell proliferation and eventual apoptotic death.

Apoptosis Detection

Figure 7A:
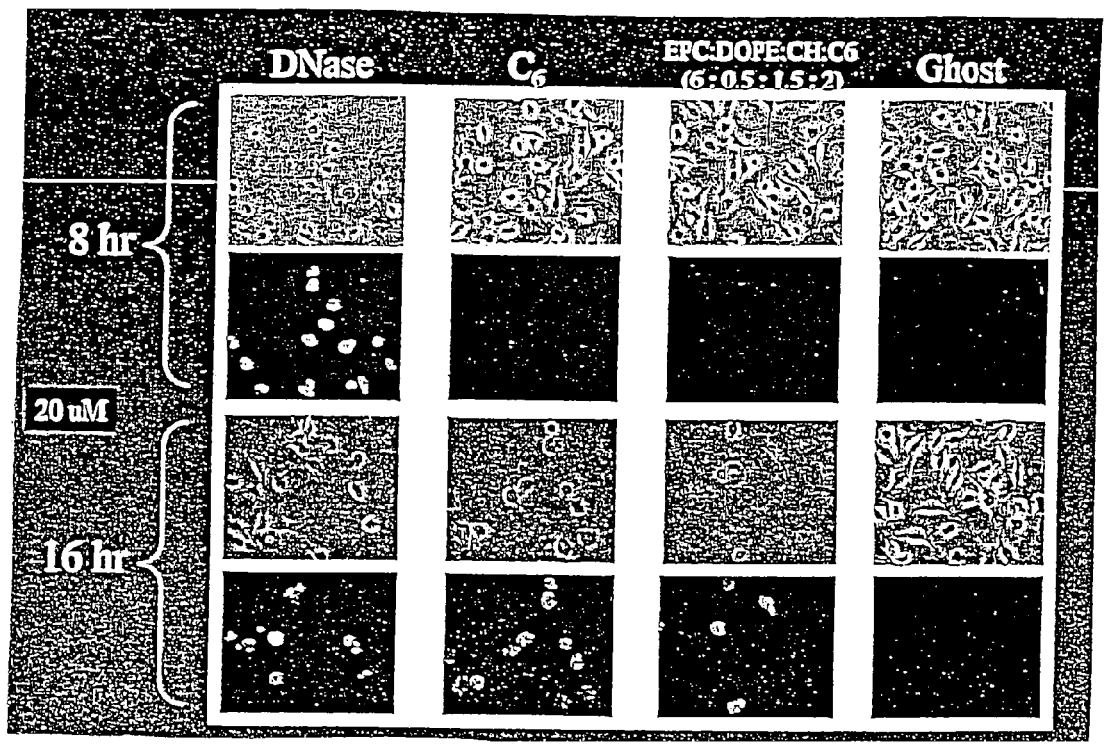
FIG. 7A. Liposomal $C_6$ delivery augments the proapoptic activity of intracellular $C_6$. TUNEL staining of fragmented 3'-OH DNA confirms that $C_6$ treatment (20 μM) induces apoptosis in MDA cells. Apoptosis was observed to occur at approximately 16 h of incubation. Nonliposomal (20 μM) $C_6$ and conventional liposomal $C_6$ [EPC/DOPE/$C_6$ (6:0.5:1.5:2)] (20 μM) induced DNA fragmentation in a similar manner to the Dnase-positive control. Liposomal $C_6$ delivery results in a significant induction of cellular apoptosis as measured by annexin V staining.

An investigation to determine whether $C_6$-dependent growth inhibition correlates with enhanced apoptosis was undertaken. To confirm that $C_6$ delivery leads to MDA cell apoptosis, TUNEL analysis (Upstate Biotechnology, Lake Placid, N.Y.) was performed, which stains cleaved DNA, a hallmark of cellular apoptosis (FIG. 7A).

TUNEL staining of cycling, serum-fed MDA cells treated with liposomal and nonliposomal $C_6$ demonstrated no DNA fragmentation at 8 h. Liposomal and nonliposomal $C_6$ treatment induced DNA fragmentation in a similar manner to the Dnase-positive control. Staining of cleaved 3'-OH DNA was observed at 16 h of treatment, a time point consistent with the in vitro pharmacokinetic profile of $C_6$ delivery. No apoptosis was observed with the Ghost formulation.

To quantitate the $C_6$-induced apoptosis, annexin V staining of treated cycling MDA cells and flow cytometry analysis of the annexin V-stained cells, using the Vybrant apoptosis assay kit (Molecular Probes, Eugene, Oreg.), was performed.

Figure 7B:
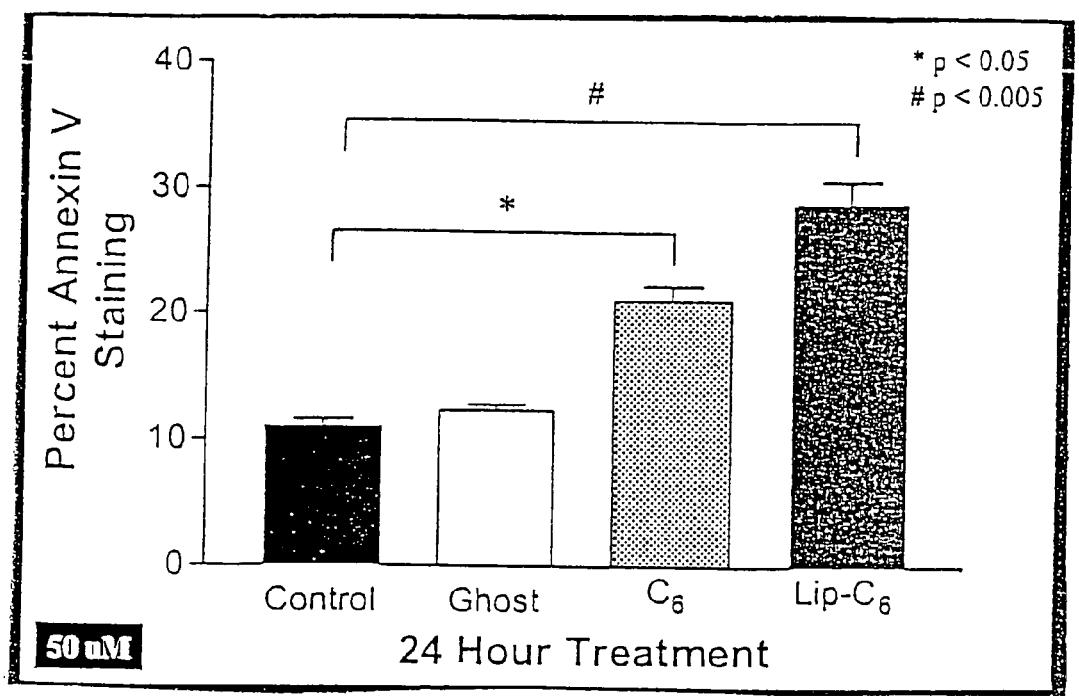
FIG. 7B. MDA cells were treated with nonliposomal $C_6$ (25 μM), pegylated liposomal $C_6$ [DOPC/DOPE/CH/PEG-C8/$C_6$ (4:3:1:1:1)] (25 μM), or Ghost liposome for 24 h, stained with FITC-annexin V, and analyzed by flow cytometry. Mean±S.E., n=3 separate experiments. *, p<0.05; # p<0.005 when compared with untreated control.

Following a 24 h treatment, pegylated liposomal $C_6$ induced a significantly greater amount of annexin V staining compared with nonliposomal $C_6$, whereas the Ghost formulation had no effect (FIG. 7B).

Assessment of Activated AKT, A Pro-Survival Kinase

Ceramide-regulated Akt signaling pathways in MDA cells treated with liposomal and $C_6$ nonliposomal formulations was investigated using Western blot analysis. Briefly, MDA cells were seeded at $4.0 \times 10^5$ cells/well in 60 mm plates and grown overnight, prior to 24-hour serum starvation. At hour 16 of serum starvation, cells were treated with liposomal or non-liposomal $C_6$ for the remainder of serum starvation. At hour 24 of serum starvation, IGF-1 (20 ng/ml) was added to cell media for a 15 minute period. Cells were washed once with cold PBS followed by the addition of 150 ul of cold lysis buffer (1% Triton X-100, 20 mM Tris, 150 mM NaCl, 1 mM EDTA, 1 mM EGTA, 2.5 mM $Na_4P_2O_7$, 1 mM β-glycerolphosphate, 1 mM $Na_3VO_4$, 1 µg/ml leupeptin in dd$H_2O$, pH 7.5) on ice. Cells were lysed for 15 minutes on ice, cell lysate was harvested, and centrifuged at 15,000×G for 15 minutes. 35 µg of protein were loaded in 4%-12% pre-casted SDS-PAGE gradient gels and probed for pAkt. Blot were stripped and re-probed for Akt-1,2,3 to demonstrate equal loading. Protein bands were visualized using ECL chemiluminescence and quantified by densitometry. The results showed that pegylated liposomal $C_6$ was more effective at reducing IGF-1-stimulated pAkt levels than was nonliposomal ceramide, whereas the Ghost formulation had no effect on pAkt levels (FIGS. 8A and 8B). Liposomal dihydro-erythro-hexanoyl-sphingosine (DHC$_6$) also displayed inhibition of IGF-1-stimulated Akt phosphorylation compared with nonliposomal DHC$_6$. Eight hours of $C_6$ treatment was selected, as this time point corresponded to near maximal accumulation of $C_6$ into MDA cells. This study supports showed that liposomal $C_6$ induced cell growth inhibition and apoptosis through long-term inhibition of Akt signaling cascades.

Confocal Studies

In order to verify cell accumulation of $C_6$ into 410.4 murine mammary adenocarcinoma cells, we administered liposomal-$C_6$ formulations with 10 molar % NBD-$C_6$ as a marker for $C_6$. Cells were counter-stained with DAPI (nuclei) and MitoTraker Red (mitochondria) for reference. $C_6$ delivery was evaluated by confocal microscopy at a magnification of 60×. Confocal microscopic images of NBD-$C_6$ delivery to cells from liposomal vesicles (FIG. 9A). NBD-$C_6$ (Green) co-localized with mitochondria (MitoTraker-Red); blue stained represents DAPI-stained nuclei.

Sucrose Gradient

The incorporation of trace amounts of [$^3$H]-$C_6$ into liposomal formulations was utilized to assess a time-dependant cellular accumulation of $C_6$ in both total cells and caveolae-enriched lipid rafts. As these lipid rafts are believed to facilitate the signal transduction of multiple pathways, including ceramide, the administration of liposomal-$C_6$ should facilitate the accumulation of $C_6$ into lipid rafts. In order to evaluate this phenomenon, a sucrose gradient (5%, 35%, and 45% sucrose) of cellular lysate was performed in order to isolate the caveolae-enriched lipid rafts. Equal aliquots of each 1 ml fraction of the gradient (total of 12 fractions) were removed and counted using a scintillation counter. Using [$^3$H]-$C_6$ as a marker for total $C_6$, liposomal delivery resulted in a time-dependant accumulation of ceramide in caveolae lipid signaling rafts (FIG. 9B). Ceramide accumulated in fractions No. 4 and 5 of a sucrose gradient, which represented caveolin-1 enriched lipid rafts (caveolae). (FIG. 9B)

In Vivo Summary

Using an in vivo mouse model system of breast adenocarcinoma, a method was established for systemic delivery of $C_6$ for the treatment of solid tumors. In vivo data suggest promising anti-cancer activity with pegylated liposomal formulations in 410.4 tumor-bearing BALB/c mice (FIG. 10A-B). These in vivo results show a dose-responsive reduction in tumor volume with liposomal $C_6$, compared to empty Ghost liposomes. This is the first study demonstrating any efficacy of systemic $C_6$ formulations in an in vivo model of tumorigenesis. Moreover, in vivo pharmacokinetic analysis demonstrated that systemic liposomal $C_6$ delivery resulted in the attainment and maintenance of steady state bioactive concentrations of $C_6$ in tumor tissue over a 24 hour period (FIGS. 11A-B). This steady state bioactive concentration was maintained although $C_6$ was rapidly cleared from the blood and major first-pass organs. Taken together, it is shown that systemic formulations of $C_6$ displayed efficacy both in vitro and in vivo with favorable pharmacokinetics. Moreover, using Swiss Webster mice, pegylated liposomal-$C_6$ formulations demonstrated no toxic side effects following intravenous injection of up to 100 mg/kg, whereas the injection of free $C_6$ in DMSO killed 50% of the mice at 10 mg/kg.

In Vivo Anticancer Efficacy

In order to assess the in vivo efficacy of systemic liposomal-$C_6$ delivery, $5 \times 10^6$ 410.4 cells were injected subcutaneously into the right hind flank of Balb/C mice. Four days following the injection of 410.4 cells, mice were injected intravenously (i.v.) with either liposomal-$C_6$, empty liposomes (Ghost), or 0.9% NaCl. Mice were treated every two days. Immediately prior to treatment, mice were weighed and tumors were measured. Tumor size was measured with calipers and tumor volume was calculated using the formula for a hemiellipsoid: $V = \pi/6 \times L \times W^2$, where V=tumor volume, L=length, and W=width.

In Vivo Pharmacokinetics

Liposomal-C6 [DSPC/DOPE/DSPC-PEG(5000)/$C_8$—PEG(750)/$C_6$-ceramide (3.75:1.75:0.75:0.75:3.0)] delivery displayed dose-dependent anti-tumor activity via ceramide-induced apoptosis. Systemic delivery of liposomal-$C_6$ inhibited tumor growth in a dose-dependent manner, compared to empty ghost liposomes (FIG. 10A). Tumors were removed following one week of treatment with 40 mg/kg liposomal-$C_6$ and cryo-sections were generated for histological analysis (FIG. 10B). Tumor sections were stained with a TUNEL Kit to assess the degree of induced apoptosis; DAPI-stained nuclei.

In Vivo Pharmacokinetics

Using [H]-$C_6$ as a marker for $C_6$ delivery, tumor-bearing mice were injected with 10 and 40 mg/kg liposomal-$C_6$, and blood, tumors, spleen, kidney, liver, and heart tissue were removed at chosen timepoints. Tissues were weighed, solubilized, and counted using a scintillation counter. The mass of total $C_6$ per mg of tissue (or ml of blood) was calculated for each tissue taken and a pharmacokinetic profile was evaluated. In order to trace the delivery of liposomal vehicles relative to the distribution of $C_6$, [$^3$H]-CHE was incorporated into liposomal formulations as a marker for the delivery vehicles.

Doses of 10 and 40 mg/kg liposomal-$C_6$ appeared to follow first order kinetics, with a sufficient plasma concentration correlating to the in vitro $IC_{50}$ sustained at 24 hours (FIG. 11A). At these doses, a steady-state concentration of $C_6$ in the tumor tissue was achieved at approximately 30 minutes (FIG. 11B). The 40 mg/kg dose maintained a concentration well above the desired $IC_{50}$ up to 24 hours. Using [$^3$H]-CHE as a marker for the pegylated liposomal vehicle, the liposomes appeared to accumulated in the tumor tissue in a time dependent manner. This may signify that the steady state concentrations of $C_6$ in tumor tissue may be sustained due to continued accumulation of the pegylated liposomes, thus replenishing metabolized $C_6$ in the tumors.

EXAMPLE 2

Dendrimers as a $C_6$-Ceramide Drug Delivery Vehicle

Dendrimer Synthesis

Dendrimers were synthesized by conjugating poly(L-lysine) (PLL) dendron with PNIPAAM grafted with PLLA. PNIPAAM grafted with PLLA was synthesized by free radical polymerization. (FIG. 12).

Dendrimer Thermo-responsive Properties

UV-vis spectroscopy (Perkin Elmer Lamda 25, Shelton, Conn.) was used to study the transmittances of dendrimers at 500 nm in PBS (pH=7.4) with temperature increase at 1° C./30 min at various concentrations (FIG. 13A). The dendrimers were thermo-responsive, showing a lower critical solution temperature (LCST) (defined as temperature at 95% of maximum transmittance) of 31, 32, 34, and 39° C. at concentrations of 1, 0.5, 0.1, and 0.05 mg·ml$^{-1}$, respectively. The LCST became obscure with decreasing concentration of the dendrimers. Above the LCST, the transmittance magnitudes decreased with increasing concentration due to the increase of the interactions of the polymers. The LCST of the PNIPAAM and the PNIPAAM grafted with PLLA decreased linearly with logarithmic concentration, and the latter was 2° C. lower than the former over the concentrations, due to the hydrophobicity of the PLLA. However, when PLL was conjugated at both ends of the PNIPAAM grafted with PLLA, the LCST of the dendrimer showed a non-linear relationship with logarithmic concentration and the highest value compared to that of other two types of polymers, due to the positive charges and hydrophilicity of the PLL.

The thermo-responsive properties of the dendrimers were confirmed further by measuring hydrodynamic sizes of the dendrimers against temperature using dynamic light scattering (DLS) (ALV, Germany). The apparent hydrodynamic diameters ($D_h$) of the dendrimers in PBS (pH=7.4) at three concentrations 1, 0.5 and 0.1 mg·ml$^{-1}$ showed a temperature dependence in three regions, respectively (data not shown). In the lower temperature range, $D_h$ decreased slightly as the solution temperature increased, reflecting the contraction of individual chains. In the middle temperature range, $D_h$ increased before reaching their maximum values, showing that the dendrimer nanoparticles aggregated with each other due to interchain association. In the higher temperature range, $D_h$ decreased as the aggregation temperature increased due to intrachain contraction. The LCST of the dendrimers was 29, 30 and 31° C., defined as the initial break points of the $D_h$-temperature curves, at three concentrations: 1, 0.5 and 0.1 mg·ml$^{-1}$, respectively. In both the lower and middle temperature ranges, $D_h$ increased with increasing concentrations because interchain interactions also increased with increasing concentrations. The LCST determined by the DLS was slightly lower than that determined by the UV-vis spectroscopy for the same solution concentration, attributed to different instruments for the measurement. Both the DLS and UV-vis results demonstrated that the LCST decreased with increasing concentrations.

Dendrimer Degradation Properties $C_6$ Ceramide and Bio-Smart Nanodendrimers

Dynamic degradation of dendrimers in PBS (pH=7.4) at 1 mg·ml$^{-1}$ at a temperature below and above the LCST, 25 and 37° C., respectively, was probed by measuring molar mass changes of the dendrimers as a function of time using MALDI-TOF. The number molar mass ($M_n$) of the dendrimers decreased with time for up to one month, and decreased faster at 37° C. than at 25° C., and reached a relatively stable value after 19 days at both temperatures. Interestingly, the stable $M_n$ after 19 days, was around 2700 g·mol$^{-1}$, and its subtraction from the initial $M_n$ (around 4200 g·mol$^{-1}$) was around 1500 g·mol$^{-1}$, which was equal to that of the PLLA. The results suggest that the dendrimers degraded, and their degradation might be attributed to the hydrolytical degradation of the PLLA component of the dendrimers. To support the above statement, the FTIR spectra and viscosity of the dendrimers as a function of time were measured, respectively (data not shown). It was observed that the peak intensities at ~1760 cm$^{-1}$, which was due to the ester C=O stretching of PLLA, clearly decreased with time and disappeared after 19 days. Because the peaks at ~1660 cm$^{-1}$, which was attributed to amide C=O stretching of PNIPAAM and PLL were relatively stable, they were used as reference peaks to normalize the peak intensities at ~1760 cm$^{-1}$. The resultant peak height percentage decreased with time and became 0 after 19 days (data not shown). Additionally, it was observed that the viscosity of the dendrimer (measured by a Cannon-Ubbelohde type viscometer, following the procedures of ASTM D 445 and ISO 3104) decreased with time, decreased faster at 37° C. than at 25° C., and reached a stable value after 19 days (data not shown). Therefore, the FTIR results, together with the viscometer and MALDI-TOF results, strongly suggested that the designed dendrimers were biodegradable due to the hydrolytic degradation of the PLLA component.

Methodology for $C_6$ loading efficiency. $C_6$ was mixed with the dendrimer at a ratio of 3:1 ($C_6$: dendrimer, w/w) in a solvent system comprised of distilled water, ethanol and N-dimethylformamide (DMF) (distilled water/ethanol/DMF (5:5:3, v/v/v) at a concentration of 1 mg/ml, and was sealed and stored at room temperature for 7 h. The $C_6$/dendrimer solution was put into a cellulose membrane (MWCO-3500) and dialyzed against ethanol (50 ml) to remove free $C_6$ from inside the membrane. The amount of $C_6$ inside and outside the cellulose membrane was measured by MALDI-TOF mass spectrophotometry. Both solutions inside and outside the membrane were mixed with a matrix solution of 2,5-dihydroxybenzoic acid at 1:9 (sample:matrix). $C_{16}$-ceramide ($C_{16}$) was used as an internal standard material and added to each solution. The amount of $C_6$, as a function of time (2, 4, 6, and 10 h.), was calculated by the relative intensity of $C_6$ and $C_{16}$ mass peaks at 424 and 562 m/z, respectively. Loading of $C_6$ into dendrimers at a ratio of 3:1 ($C_6$:dendrimer) resulted in a loading efficiency of approximately 35.9±1.2%.

Methodology for $C_6$ release from dendrimers. In order to assess the interaction between $C_6$ and the dendrimer, it is necessary to evaluate the release kinetics of $C_6$ from the dendrimer. The fractional release of $C_6$ ($M_t/W_\infty$, where $M_t$ and $W_\infty$ are the amount of the $C_6$ released at time t and the maximum amount of $C_6$ released, respectively) increased with time due to the hydrolytic degradation of the dendrimer. The dendrimer-$C_6$ complex was dissolved in sterile PBS (pH=7.4) and put into a cellulose membrane (MWCO=3500) and dialyzed against sterile PBS (pH=7.4) (50 ml) containing sodium dodecyl sulfate (SDS) at 0.5% (w/v). Since $C_6$ is extremely hydrophobic, it was essential to perform the dialysis in the presence of a detergent, such as SDS. Final concentrations of the dendrimer was 0.1 mg/ml with continuous magnetic stirring at temperatures below (25° C.) and above the LCST (37° C.). At selected time intervals (between 0 and 30 days), 1 ml buffer solution was removed and replaced with fresh buffer, in order to determine the concentration of the released $C_6$. In order to quantitate $C_6$-release from the dendrimer, the amount of $C_6$ inside and outside the cellulose membrane was measured by MALDI-TOF mass spectrophotometry, using $C_{16}$ as an internal standard. At 37° C., a temperature above the LCST of the dendrimer, the dendrimer is more hydrophobic, thus resulting in a slower release profile of $C_6$ from the $C_6$-loaded dendrimer (FIG. 13B).

Dendrimers as a Drug Delivery Vehicle for $C_6$-ceramide
Dendrimer Degradation Properties
Design of Dendrimers with an LCST Above Physiologic Temperature The primary objective is directed at generating biodegradable and temperature-sensitive dendritic nanoparticles that can be complexed to $C_6$, are injected intravenously, are soluble in the blood stream for a long period of time, and achieve targeted and sustained delivery of therapeutic agents to solid tumors. In order to create dendrimers with a LCST of approximately 40° C. for thermally targeting the dendrimers to solid tumors, the relative molar ratios between NIPAAM, hydrophobic PLLA and hydrophilic PLL play a critical role. It is well known that the homopolymer PNIPAAM has a LCST of 32° C. {Eeckman, 2001 #52}. This LCST will decrease or increase by increasing the amount of the incorporated hydrophobic or hydrophilic component, respectively{Eeckman, 2001 #52}.

The dendrimer structure was optimized in order to engineer bio-responsive, smart dendrimers that will release $C_6$ upon the induction of local hyperthermia above physiological temperature. In order to design a dendrimer with an optimal LCST slightly above 37° C., we have replaced PLLA with a more flexible and amorphous polymer, such as poly(D,L-lactic acid) (PDLLA) with molar masses 800, 2000 and 4000 g/mol. Secondly, we used different generations (successive concentric rings of dendritic structure) of PLL, such as 3, 4 or 5. Finally, we used different molar ratios between PDLLA macromer and NIPAAM monomer, such as 0.02, 0.05 and 0.1 mol %. The LCSTs of the resulting dendrimers can be assessed by UVvis spectroscopy by measuring transmittance as a function of temperature and light scattering by measuring hydrodynamic size as a function of temperature.

The LCST of the dendrimers was increased by copolymerization with N-isopropylmethacrylamide (NIMAAM). The resulting core-copolymers exhibited the LCST of 36, 42, and 44° C. with increasing NIMAAM monomer at 50, 60, and 70% of NIPAAM monomers, respectively. In this way, we have designed bio-smart dendrimers that can be engineered to release hydrophobic chemotherapeutic agents, including growth-arresting, pro-apoptotic lipid-derived second messengers to solid tumors through targeting the tumor via local hyperthermia. Localized heat may be applied using ultrasound or heat patch devices to elevate the local tumor temperature above the LCST of the dendrimers. This process is coined as "physiological hyperthermic drug delivery."

Dendrimer Cell Viability

Due to the advantages that polymeric nanoparticles have compared to liposomal technologies as discussed above, we have loaded $C_6$ into temperature-sensitive dendrimer nanoparticles in order to target solid tumors using a temperature-induced delivery strategy. Our proprietary dendrimer nanoparticles are comprised of PLLA, PLL, and PNIMPAM. As stated above, using UV-vis spectroscopy to monitor the dendrimer solution transmittance with increasing temperature, we observed a sharp transition, confirming that these dendrimers are indeed thermoresponsive. The approximate LCST for these prototypic dendrimers was found to be approximately 34° C. at 100 µg/ml. Using MALDI-TOF mass spectrophotometry, we demonstrated that the molar mass of the dendrimers decreased with time, verifying that they are also biodegradable. As analyzed by confocal microscopy, the dendrimers preferentially accumulate into MDA cells at a temperature above the LCST (37° C.) than below the LCST (25° C.) (FIG. 14A), likely due to increased hydrophobicity. Moreover, using flow cytometry to quantitate the intracellular accumulation and uptake of FITC-labeled dendrimers, we demonstrated that significantly more dendrimer uptake results in MDA cells at a temperature above the LCST (37° C.) than below the LCST (25° C.). (FIG. 14B). More importantly, treatment of MDA cells with these $C_6$-loaded dendrimers resulted in the significant growth inhibition/cytotoxicity, while dendrimer alone displayed no cytotoxicity (FIG. 15A). In addition to inducing growth arrest, C6-enriched dendrimers induced apoptosis of MDA cells (FIG. 15B). Taken together, our preliminary data demonstrate that the dendrimers effectively control release of an anti-cancer drug $C_6$. Optimization of this embodiment has included the design of polymeric dendrimers with an LCST slightly above physiological temperature, to allow for physiological hyperthermic drug delivery.

The following example is further illustrative.

EXAMPLE 3

Synthesis of Ceramide-containing Calcium Phospho-Silicate Shell Resorbable Nanoparticles for Systemic Delivery Reverse micelles were prepared using the nonionic surfactant poly(oxyethylene) nonylphenyl ether (Igepal CO-520, Aldrich Chemical Co.) without further purification. Cyclohexane, deionized water and $C_6$-ceramide was used as received for the synthesis.

Microemulsions of 20 mL total volume, consisting of 4 mL Igepal, 10 mL cyclohexane and deionized water, were prepared at ambient temperature in a 30 mL vial with rapid stirring. This produced a uniform mixture to which trace amounts of $C_6$ was added in an aqueous phase as a micellular mixture of water and drug. The resulting micelle structure containing $C_6$ was coated with CPS having composition $Ca_x(PO_4)_y zSiO_2$, where $0.1 \le x \le 10$ 0.1, $0.1 \le y \le 10$, and $0 \le z \le 10$. The size of the resulting nanoparticles was controlled by varying the ratio of water to surfactant (R=[water]/[surfactant].

After the reverse micelles were encapsulated in the CPS coating, the nanoparticles were washed and concentrated using size exclusion high performance liquid chromatography (SEC) modified specifically for the $C_6$-containing shell nanoparticles. An elution column shorter than normal which contains microporous silica particles having a diameter of about 20 microns diameter was utilized in which ethanol is added as the elution solvent. To disperse the nanoparticles, an alkylamine silane coupling agent, aminopropyltrichlorosilane, was added to the suspension. This coupling agent also was added to the microporous silica particles used to pack the SEC column. The pH of the suspended nanoparticles was maintained at approximately 7.0 by adding acetic acid or sodium hydroxide as needed. Additionally, a carbodiimide-mediated polyethylene glycol (PEG) coupling agent was attached to the alkylamine coupling agent.

EXAMPLE 4

Hydrogels as $C_6$-Ceramide Release Vehicles

Figure 16:
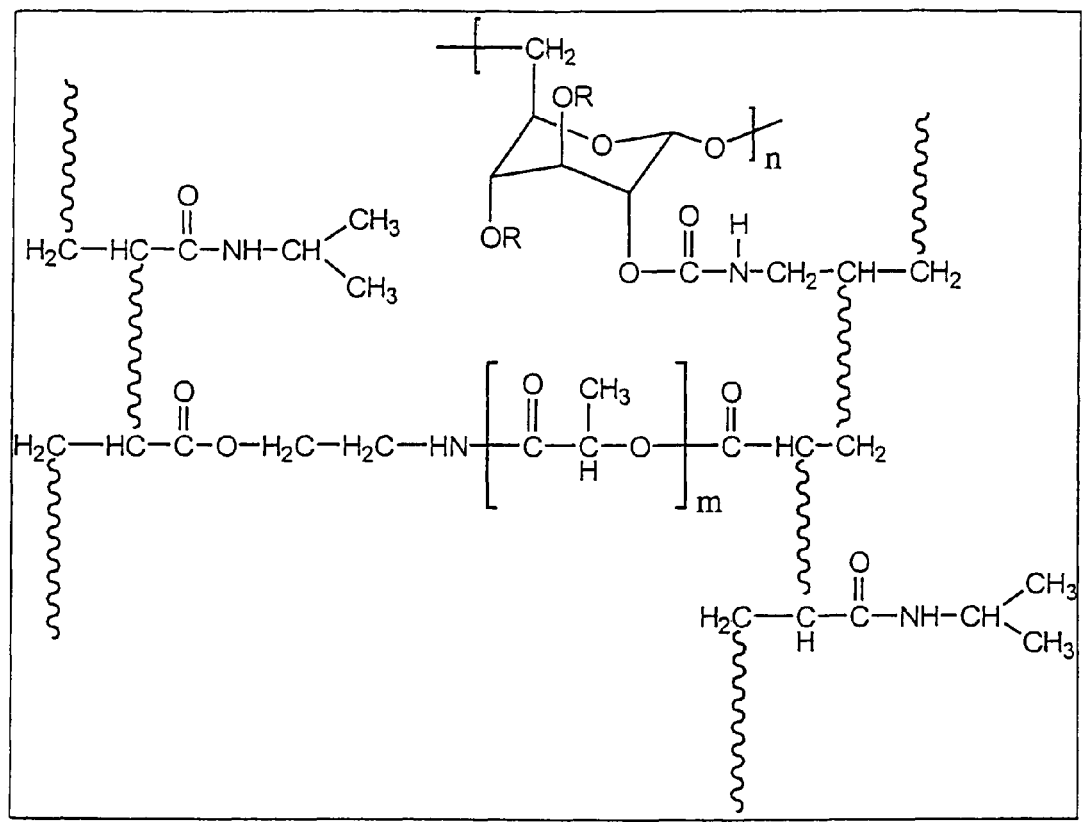
FIG. 16. Structure of NIPAAM-co-PLLA-co-dextran hydrogels, wherein R is a —CONHCH$_2$CH=CH$_2$ or H, and m and n integers from about 1 to several thousand. The NIPAAM segment can also have units of from about 10 to several thousand.

Nine multifunctional hydrogels with both thermoresponsive and biodegradable properties were synthesized and characterized. The hydrogels are copolymeric networks composed of N-isopropylacrylamide (NIPAAM) as a thermoresponsive component, poly(L-lactic acid) (PLLA) as a hydrolytically degradable and hydrophobic component, and dextran as an enzymatically degradable and hydrophilic component. Due to their multifunctional properties, the designed hydrogels are suitable for biomedical applications including drug delivery and tissue engineering. (FIG. 16.)

The hydrogels showed thermoresponsive properties and the LCST was around 32° C., typical to that of PNIPAAM. The hydrogels were also hydrolytically biodegradable with pore sizes increasing after about 4 months. The swelling behaviors of the hydrogels were different at temperature above (37° C.) and below (25° C.) the LCST and strongly depended on the hydrophilicity and hydrophobicity of the copolymers. In conclusion, the hydrogels have great potential for a controlled and sustained release of $C_6$-ceramide through changing their copolymer compositions and thermo-responsive and biodegradable properties.

It should be understood that the examples and embodiments described herein are for illustrative purposes only and that various modifications or changes in light thereof will be suggested to persons skilled in the art and are to be included within the spirit and purview of this application.

The invention claimed is:

1. A resorbable unagglomerated nanoparticle drug delivery vehicle for delivering a growth-arresting lipid-derived bioactive compound and/or a hydrophobic chemotherapeutic agent and/or gene therapy agent to an animal or human in need of such delivery, comprising a dispersant attached to a calcium phospho-silicate shell encapsulating the lipid-derived compound, hydrophobic chemotherapeutic agent or gene therapy agent, wherein the lipid-derived compound is selected from the group consisting of C2-C10 ceramides and C18-C24 ceramides, dimethyl sphingosine, trimethyl sphingosine, ether-linked diglycerides, ether-linked phosphatidic acids, sphingosines and sphinganines; and the gene therapy agent is selected from the group consisting of oligonucleotides, ribozymes, DNA-zymes, plasmids, antisense or Si-RNA therein.

2. The resorbable unagglomerated nanoparticle drug delivery vehicle of claim 1, wherein the dispersant is selected from the group consisting of citric acid, tartaric acid, acetic acid, aminopropyltrichlorosilane, 3-aminopropyltrimethoxysilane (APS), 3-aminopropylsilsesquioxane, 3-glycidoxypropyl-trimethoxysilane (GPS), trimethoxysilyl-propyldiethylen-etriamine (DETA), 3-trimethoxysilypropylsuccinic anhydride, and alkylcarboxylic acid silane coupling agents.

3. The resorbable unagglomerated nanoparticle drug delivery vehicle of claim 2, wherein a carbodiimide-mediated polyethylene glycol (PEG) coupling agent is added to the dispersant in order to provide an attachment point for binders.

4. A method of administering a composition to an animal or human in need thereof, comprising administering a composition comprising the resorbable unagglomerated nanoparticle drug delivery vehicle of claim 1 to the animal or human, wherein the growth-arresting lipid-derived bioactive compound or gene therapy agent contained therein is in a concentration of up to approximately 1000 mg ml$^{-1}$.

5. The method of claim 4 wherein the growth-arresting lipid-derived bioactive compound and/or a hydrophobic chemotherapeutic agent and/or gene therapy agent comprises at least approximately 40 wt % of the composition.

6. A resorbable unagglomerated nanoparticle for delivering a growth-arresting lipid-derived bioactive compound and/or a hydrophobic chemotherapeutic agent and/or gene therapy agent to an animal or human in need of such delivery, comprising a dispersant attached to a calcium phospho-silicate shell encapsulating the lipid-derived compound, hydrophobic chemotherapeutic agent or gene therapy agent, wherein the lipid-derived compound is selected from the group consisting of C2-C24 ceramides, dimethyl sphingosine, trimethyl sphingosine, ether-linked diglycerides, ether-linked phosphatidic acids, sphingosines and sphinganines and the gene therapy agent is selected from the group consisting of oligonucleotides, ribozymes, DNA-zymes, plasmids, antisense or Si-RNA therein.

7. The resorbable unagglomerated nanoparticle of claim 6 having a diameter ranging from between about 1 to 300 nm.

8. The resorbable unagglomerated nanoparticle drug delivery vehicle of claim 7, wherein the resorbable unagglomerated nanoparticles have a diameter of about 20 nm or less.

9. The resorbable unagglomerated nanoparticle of claim 6 having a diameter less than 50 nm.

10. The resorbable unagglomerated nanoparticle of claim 9 having a diameter of about 20 nm or less.

11. The resorbable unagglomerated nanoparticle of claim 6, wherein the dispersant is selected from the group consisting of citric acid, tartaric acid, acetic acid, aminopropyltrichlorosilane, 3-aminopropyltrimethoxysilane (APS), 3-aminopropylsilsesquioxane, 3-glycidoxypropyl-trimethoxysilane (GPS), trimethoxysilyl-propyldiethylenetriamine (DETA), 3-trimethoxysilypropylsuccinic anhydride, and alkylcarboxylic acid silane coupling agents.

12. The resorbable unagglomerated nanoparticle of claim 11, wherein a carbodiimide-mediated polyethylene glycol (PEG) coupling agent is added to the dispersant in order to provide an attachment point for binders.

13. The resorbable unagglomerated nanoparticle of claim 11 wherein the alkylcarboxylic acid silane coupling agents are amide linked carboxyl groups.

14. The resorbable unagglomerated nanoparticle of claim 12 wherein the binders are antibodies.

* * * * *